(12) United States Patent
Yazdani et al.

(10) Patent No.: US 10,526,593 B2
(45) Date of Patent: Jan. 7, 2020

(54) METHOD FOR OBTAINING A COMPOSITION FOR BIOMASS HYDROLYSIS

(71) Applicants: INTERNATIONAL CENTRE FOR GENETIC ENGINEERING & BIOTECHNOLOGY, New Delhi (IN); DEPARTMENT OF BIOTECHNOLOGY MINISTRY OF SCIENCE & TECHNOLOGY, New Delhi (IN)

(72) Inventors: Syed Shams Yazdani, New Delhi (IN); Funso Emmanuel Ogunmolu, New Delhi (IN)

(73) Assignees: International Centre For Genetic Engineering & Biotechnology, New Delhi (IN); Department of Biotechnology Ministry of Science & Technology, New Delhi (IN)

( * ) Notice: Subject to any disclaimer, the term of this patent is extended or adjusted under 35 U.S.C. 154(b) by 0 days.

(21) Appl. No.: 15/742,892

(22) PCT Filed: Jul. 8, 2016

(86) PCT No.: PCT/IN2016/050225
§ 371 (c)(1),
(2) Date: Jan. 9, 2018

(87) PCT Pub. No.: WO2017/006352
PCT Pub. Date: Jan. 12, 2017

(65) Prior Publication Data
US 2019/0032037 A1    Jan. 31, 2019

(30) Foreign Application Priority Data
Jul. 9, 2015 (IN) ............ 1714/DEL/2015

(51) Int. Cl.
| | | |
|---|---|---|
| C12N 1/20 | (2006.01) |
| C12N 9/24 | (2006.01) |
| C12N 9/42 | (2006.01) |
| C12N 9/18 | (2006.01) |
| C12N 9/34 | (2006.01) |

(52) U.S. Cl.
CPC ............ *C12N 9/2402* (2013.01); *C12N 9/18* (2013.01); *C12N 9/248* (2013.01); *C12N 9/2428* (2013.01); *C12N 9/2437* (2013.01); *C12N 9/2445* (2013.01); *C12N 9/2482* (2013.01); *C12Y 301/01072* (2013.01); *C12Y 302/01* (2013.01); *C12Y 302/01003* (2013.01); *C12Y 302/01004* (2013.01); *C12Y 302/01008* (2013.01); *C12Y 302/01021* (2013.01); *C12Y 302/01055* (2013.01); *C12Y 302/01091* (2013.01); *C12P 2203/00* (2013.01); *Y02E 50/16* (2013.01)

(58) Field of Classification Search
USPC .................................................. 424/94.6
See application file for complete search history.

(56) References Cited

PUBLICATIONS

Guais, Olivier et al. (2008) Journal of industrial Microbiology and biotechnology vol. 35, No. 12, pp. 1659-1668.*

* cited by examiner

Primary Examiner — Tekchand Saidha
(74) Attorney, Agent, or Firm — Mark M. Friedman

(57) ABSTRACT

The present invention discloses a composition for biomass hydrolysis. The components of the composition may be obtained by biological or synthetic means. Synthetically, the components of the composition of the present invention may be obtained by amino acid synthesis or may be procured commercially.

11 Claims, 12 Drawing Sheets
Specification includes a Sequence Listing.

SEQUENCE LISTING

<160> NUMBER OF SEQ ID NOS: 16

<210> SEQ ID NO 1
<211> LENGTH: 529
<212> TYPE: PRT
<213> ORGANISM: Penicillium funiculosum

<400> SEQUENCE: 1

```
Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Ser Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ala Asn Asn Ala Asn Thr Gly
    210                 215                 220

Ile Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Phe Thr Val Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
                325                 330                 335

Val Val Ile Pro Gln Pro Ser Ser Lys Ile Ser Gly Ile Ser Gly Asn
            340                 345                 350

Val Ile Asn Ser Asp Tyr Cys Ala Ala Glu Ile Ser Thr Phe Gly Gly
        355                 360                 365
```

```
Thr Ala Ser Phe Ser Lys His Gly Gly Leu Thr Asn Met Ala Ala Gly
        370                 375                 380

Met Glu Ala Gly Met Val Leu Val Met Ser Leu Trp Asp Asp Tyr Ala
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Thr Cys Ala Thr Thr Ser Gly Asp Pro
            420                 425                 430

Lys Thr Val Glu Ser Gln Ser Gly Ser Ser Tyr Val Thr Phe Ser Asp
                435                 440                 445

Ile Arg Val Gly Pro Phe Asn Ser Thr Phe Ser Gly Gly Ser Ser Thr
        450                 455                 460

Gly Gly Ser Thr Thr Thr Thr Ala Ser Arg Thr Thr Thr Thr Ser Ala
465                 470                 475                 480

Ser Ser Thr Ser Thr Ser Ser Thr Ser Thr Gly Thr Gly Val Ala Gly
                485                 490                 495

His Trp Gly Gln Cys Gly Gly Gln Gly Trp Thr Gly Pro Thr Thr Cys
        500                 505                 510

Val Ser Gly Thr Thr Cys Thr Val Val Asn Pro Tyr Tyr Ser Gln Cys
                515                 520                 525

Leu
```

<210> SEQ ID NO 2
<211> LENGTH: 733
<212> TYPE: PRT
<213> ORGANISM: Penicillium funiculosum

<400> SEQUENCE: 2

```
Met Tyr Ser Ala Phe Leu Leu Leu Ala Ser Ala Thr Pro Ile Val
1               5                   10                  15

Ser Ala Gln Ser Ala Ser Trp Ser Ala Ala Tyr Ser Lys Ala Thr Ala
                20                  25                  30

Ala Leu Ser Lys Leu Ser Gln Asn Asp Lys Ile Gly Met Val Thr Gly
            35                  40                  45

Val Gly Trp Gly Lys Gly Pro Cys Val Gly Asn Thr Ala Ala Pro Ser
50                  55                  60

Gly Ile Ser Phe Pro Ser Leu Cys Ile Gln Asp Ser Pro Leu Gly Val
65                  70                  75                  80

Arg Tyr Ala Asn Pro Val Thr Ala Phe Pro Ala Gly Thr Asn Ala Gly
                85                  90                  95

Met Thr Trp Asp Arg Thr Leu Met Asn Gln Arg Gly Ala Ala Leu Gly
            100                 105                 110

Ala Glu Ser Lys Gly Leu Gly Val His Val Gln Leu Gly Pro Val Ala
            115                 120                 125

Gly Pro Leu Gly Lys Ile Ala Gln Gly Gly Arg Gly Trp Glu Gly Phe
130                 135                 140

Gly Thr Asp Pro Tyr Leu Ser Gly Val Ala Met Ile Glu Thr Ile Thr
145                 150                 155                 160

Gly Met Gln Ser Ser Gly Thr Gln Ala Cys Ala Lys His Tyr Ile Gly
                165                 170                 175

Asn Glu Gln Glu Leu Asn Arg Glu Ser Met Ser Ser Asn Ile Asp Asp
            180                 185                 190

Arg Thr Leu His Glu Leu Tyr Leu Trp Pro Phe Ala Asp Ala Val Arg
            195                 200                 205
```

```
Ala Asn Val Ala Ser Val Met Cys Ser Tyr Asn Gln Ile Asn Gly Thr
            210                 215                 220

Phe Ser Cys Glu Asn Glu Glu Ser Met Thr Gly Ile Leu Lys Thr Glu
225                 230                 235                 240

Leu Gly Phe Pro Gly Tyr Ile Met Ser Asp Trp Asp Ala Gln His Thr
                    245                 250                 255

Thr Val Thr Ser Ala Asn Ser Gly Leu Asp Met Thr Met Pro Gly Ser
            260                 265                 270

Asp Tyr Ser Asp Thr Pro Ser Ser Val Leu Trp Gly Gln Asn Leu Ala
        275                 280                 285

Asn Ala Ile Ser Ser Gly Gln Val Ala Gln Ser Arg Leu Asp Asp Met
290                 295                 300

Val Thr Arg Ile Leu Ala Ala Trp Tyr Leu Val Gly Gln Asp Gln Gly
305                 310                 315                 320

Phe Pro Ala Val Ala Phe Asn Ser Trp Thr Gly Gly Gln Ala Ser Val
                325                 330                 335

Asn Val Thr Ser Asn His Asn Gln Val Ala Arg Ala Val Ala Arg Asp
            340                 345                 350

Ser Ile Val Leu Leu Lys Asn Thr Asn Ser Thr Leu Pro Leu Asn Lys
        355                 360                 365

Pro Ser Ser Ile Ala Ile Ile Gly Thr Asp Ala Gln Thr Asn Pro Ser
370                 375                 380

Gly Pro Asn Ala Cys Thr Asp Arg Gly Cys Asp Thr Gly Thr Leu Ala
385                 390                 395                 400

Met Gly Trp Gly Ser Gly Thr Cys Gln Phe Pro Tyr Leu Thr Asp Pro
                405                 410                 415

Leu Thr Ala Ile Lys Thr Arg Ala Ala Ser Asp Gly Thr Thr Ile Thr
            420                 425                 430

Thr Ser Ile Ser Asp Asn Gly Ser Ala Gly Ala Ser Val Ala Gln Ser
        435                 440                 445

Ala Glu Tyr Ala Ile Val Phe Ile Asn Ser Asp Ser Gly Glu Gly Tyr
450                 455                 460

Ile Thr Val Glu Gly Val Ala Gly Asp Arg Asn Asn Leu Asp Pro Trp
465                 470                 475                 480

His Ser Gly Asn Ala Leu Val Gln Ser Val Ala Ala Val Asn Lys Lys
                485                 490                 495

Thr Ile Val Val Ile His Ser Val Gly Pro Val Ile Leu Glu Thr Ile
            500                 505                 510

Leu Ala Gln Pro Asn Val Val Ala Val Val Trp Ala Gly Ile Pro Gly
        515                 520                 525

Gln Glu Ser Gly Ser Ala Leu Thr Asp Ile Leu Tyr Gly Ser Thr Ala
530                 535                 540

Pro Ser Gly Lys Leu Thr Tyr Thr Ile Ala Lys Gln Ala Ser Asp Tyr
545                 550                 555                 560

Gly Thr Ala Val Val Ser Gly Ser Asp Asn Tyr Pro Glu Gly Leu Phe
                565                 570                 575

Ile Asp Tyr Arg His Phe Asp Lys Ser Asn Ile Glu Pro Arg Tyr Glu
            580                 585                 590

Phe Gly Tyr Gly Leu Ser Tyr Thr Phe Gly Tyr Thr Asn Leu Ala
        595                 600                 605

Ile Asp Ile Thr Val Ser Thr Gly Pro Thr Thr Gly Gln Thr Val Pro
610                 615                 620

Gly Gly Pro Ser Asp Leu Phe Glu Ser Val Gly Thr Val Thr Val Gln
```

```
            625                 630                 635                 640
Val Ala Asn Thr Gly Ser Val Ala Gly Ser Glu Val Ala Gln Leu Tyr
                    645                 650                 655

Ile Gly Leu Pro Ser Ser Ala Pro Ser Ser Pro Lys Gln Leu Arg
                660                 665                 670

Gly Phe Asp Lys Leu Ser Leu Ala Gly Ala Ser Gly Thr Ala Thr
            675                 680                 685

Phe Asp Leu Thr Arg Arg Asp Leu Ser Tyr Trp Asp Val Ser Lys Gln
        690                 695                 700

Lys Trp Val Val Pro Ser Gly Val Phe Thr Val Tyr Val Gly Ala Ser
705                 710                 715                 720

Ser Arg Asp Ile Arg Leu Gln Gly Thr Phe Thr Val Gly
                    725                 730
```

<210> SEQ ID NO 3
<211> LENGTH: 282
<212> TYPE: PRT
<213> ORGANISM: Penicillium funiculosum

<400> SEQUENCE: 3

```
Met Gly Ile Ser Ser Ile Leu Leu Ser Ala Leu Ile Ala Gly Gly Ala
1               5                   10                  15

Leu Ala Leu Pro Ala Ala Glu Pro Val Ser Phe Asp Ile Arg Asp Glu
                20                  25                  30

Asn Ile Thr Leu Ala Arg Arg Ala Glu Ala Ile Asn Tyr Asn Gln Asn
            35                  40                  45

Tyr Ile Ala Ser Gly Ala Asn Val Gln Tyr Ser Pro Asn Ile Ala Ala
50                  55                  60

Gly Ser Phe Ser Ile Asn Tyr Asn Thr Gln Gly Asp Phe Val Val Gly
65                  70                  75                  80

Leu Gly Trp Gln Pro Gly Asp Ala Asn Pro Ile Thr Tyr Ser Gly Ser
                85                  90                  95

Phe Ser Ala Ser Gly Val Gly Ile Leu Ala Val Tyr Gly Trp Thr Thr
                100                 105                 110

Asn Pro Leu Val Glu Tyr Tyr Ile Met Glu Val His Asp Gly Tyr Gln
            115                 120                 125

Thr Val Gly Thr His Lys Gly Thr Val Thr Ser Asp Gly Gly Thr Tyr
        130                 135                 140

Asp Ile Trp Glu His Gln Gln Val Asn Gln Pro Ser Ile Leu Gly Thr
145                 150                 155                 160

Ser Thr Phe Asn Gln Tyr Ile Ser Ile Arg Gln Ser Pro Arg Thr Ser
                165                 170                 175

Gly Thr Val Thr Val Gln Asn His Phe Asn Ala Trp Ala Gln Ala Gly
                180                 185                 190

Leu Asn Leu Gly Thr Met Asn Tyr Gln Val Leu Ala Val Glu Ser Trp
            195                 200                 205

Ser Gly Ser Gly Ser Gly Gln Ile Ser Leu Ser Lys Gly Thr Gly Gly
        210                 215                 220

Gly Thr Thr Thr Thr Thr Pro Thr Gly Pro Thr Ser Thr Ser Thr Ala
225                 230                 235                 240

Pro Ser Ser Gly Gly Thr Gly Ala Ala Gln Trp Gly Gln Cys Gly Gly
                245                 250                 255

Ile Gly Trp Thr Gly Pro Thr Thr Cys Val Ser Pro Tyr Thr Cys Lys
                260                 265                 270
```

Tyr Phe Asn Ala Tyr Tyr Ser Gln Cys Gln
            275                 280

<210> SEQ ID NO 4
<211> LENGTH: 332
<212> TYPE: PRT
<213> ORGANISM: Penicillium funiculosum

<400> SEQUENCE: 4

Met Cys Lys Ser Gly Thr Met Trp Gly Glu Gln Thr Thr Val Gly Ser
1               5                   10                  15

Asp Glu Thr Trp His Tyr Ser Arg Ser Thr His Phe Gly Leu Thr Ser
            20                  25                  30

Gly Gly Ala Cys Gly Phe Gly Leu Tyr Gly Leu Cys Thr Lys Gly Ser
        35                  40                  45

Thr Thr Ala Ser Trp Thr Asp Pro Met Leu Gly Asp Thr Cys Asp Ala
    50                  55                  60

Phe Cys Thr Ala Tyr Pro Leu Leu Cys Gln Asp Pro Ser Asn Val Thr
65                  70                  75                  80

Leu Arg Gly Asn Phe Ala Ala Pro Asn Gly Asp Tyr Tyr Thr Gln Phe
                85                  90                  95

Trp Ser Ser Leu Ala Ala Glu Gly Asn Pro Asp Asn Tyr Leu Ser Cys
            100                 105                 110

Gly Glu Cys Phe Glu Leu Ile Arg Thr Lys Ser Asp Gly Thr Asp Tyr
        115                 120                 125

Thr Val Gly Glu Asp Gly Tyr Thr Asp Pro Val Tyr Leu Glu Ile Val
    130                 135                 140

Asp Ser Cys Pro Cys Ser Ala Asn Pro Lys Trp Cys Cys Gly Ser Gly
145                 150                 155                 160

Ala Asp His Cys Gly Glu Ile Asp Phe Thr Tyr Gly Cys Pro Ile Pro
                165                 170                 175

Lys Asp Ser His His Met Asp Leu Ser Asp Ile Ala Met Gly Arg Leu
            180                 185                 190

Gln Gly Asn Gly Ser Leu Ala Asp Gly Val Ile Pro Ile Arg Tyr Lys
        195                 200                 205

Arg Val Pro Cys Pro Lys Pro Gly Asn Val Tyr Leu Trp Leu Arg Asp
    210                 215                 220

Gly Ala Gly Pro Tyr Tyr Phe Ser Met Ser Ala Val Asn Thr Asn Gly
225                 230                 235                 240

Val Gly Ser Val Val Asn Ile Glu Val Gln Gly Ser Gly Gln Ser Ser
                245                 250                 255

Trp Thr Ala Leu Lys Arg Asp Pro Asn Tyr Ser Ser Ser Arg Pro Gln
            260                 265                 270

Glu Arg Tyr Gly Ala Trp Val Val Pro Gln Gly Ala Gly Pro Phe Asn
        275                 280                 285

Leu Pro Ile Gly Val Arg Ile Thr Ser Pro Asp Gly Gln Gln Ile Val
    290                 295                 300

Ser Thr Asn Val Ile Thr Ser Phe Thr Ala Pro Ala Thr Ala Pro Ser
305                 310                 315                 320

Gly Phe Trp Tyr Ile Asp Thr Gly Val Gln Phe Thr
                325                 330

<210> SEQ ID NO 5
<211> LENGTH: 158
<212> TYPE: PRT
<213> ORGANISM: Penicillium funiculosum

<400> SEQUENCE: 5

Met Val Arg Pro Gly Leu Ser Pro Gly Lys Ser Lys Ser Ile Leu Thr
1               5                   10                  15

Ile Lys Ala Asp Asn Arg Leu Tyr Thr Phe Ser Pro Glu Thr Arg Glu
            20                  25                  30

Glu Leu Arg Lys Phe Arg Leu Gly Thr Ser Arg Ala Lys Asp Pro Gln
        35                  40                  45

Ala Arg Ile Tyr Ile Ile Asp Ile Lys Thr Lys Glu Ile Arg Ala Glu
    50                  55                  60

Ser Asn Asp Thr Tyr Thr Lys Leu Glu Asp Ile Ala Asp Glu Leu Pro
65                  70                  75                  80

Asp Ser Ser Pro Arg Phe Val Leu Leu Ser Tyr Pro His Thr Leu Ala
                85                  90                  95

Ser Gly Arg Leu Ser Val Pro Tyr Val Leu Leu Tyr Tyr Leu Pro Glu
            100                 105                 110

Asn Cys Asn Pro Ser Ser Arg Met Met Tyr Ala Gly Ala Val Glu Leu
        115                 120                 125

Phe Arg Asn Thr Ala Glu Val Gln Arg Val Ile Glu Val Glu Ser Glu
    130                 135                 140

Gly Asp Val Leu Asp Ile Glu Thr Lys Leu Ser Asn Asp Lys
145                 150                 155

<210> SEQ ID NO 6
<211> LENGTH: 180
<212> TYPE: PRT
<213> ORGANISM: Penicillium funiculosum

<400> SEQUENCE: 6

Met Ala Leu Pro Thr Ser Gln Lys Arg Asp Gly Ser Thr Gly Pro Phe
1               5                   10                  15

Gly Val Leu Ala Leu Arg Ser Gly Ser Pro Ile His Leu Gln Ser Val
            20                  25                  30

Asn Ala Ala Gly Gln Arg Phe Trp Ile Gly Val Pro Thr Ala Thr Tyr
        35                  40                  45

Cys Pro Ser Glu Val Asp Pro Cys Pro Pro Gly Thr Glu Thr Val Trp
    50                  55                  60

Ala Asn Pro Asn Gly Leu Asp Val Glu Val Pro Gly Gly Gln Gln Val
65                  70                  75                  80

Tyr Val Asp Pro Ser Gly Ala Leu Ala Phe Thr Gln Ala His Ser Ala
                85                  90                  95

Asn Ile Pro Ala Gly Ala Ala Leu Gly Pro Phe Thr Phe Thr Pro Gly
            100                 105                 110

Thr Gln Phe Gly Ala Tyr Ser Thr Ser Ala Phe Gly Ala Thr Gly Phe
        115                 120                 125

Met Ala Cys Pro Asp Asp Ala Ala Asn Pro Ser Lys Trp Gln Val Phe
    130                 135                 140

Ala Ala Phe Pro Thr Ala Thr Val Pro Thr Gly Asn Val Gly Asp Cys
145                 150                 155                 160

Leu Gly Phe Asp Ala Ala Ala Pro Ala Phe Thr Gly Asp Ile Pro Ala
                165                 170                 175

Trp Gln Tyr Ile
            180

<210> SEQ ID NO 7

```
<211> LENGTH: 173
<212> TYPE: PRT
<213> ORGANISM: Penicillium funiculosum

<400> SEQUENCE: 7

Met Ile Gly Lys Ser Leu Thr Val Ala Ala Leu Leu Ser Leu Asn Leu
1               5                   10                  15

Val Ser Ala Gly Pro Ile Val Lys Arg Ser Val Leu Thr Asp Leu Gln
            20                  25                  30

Thr Val Tyr Ser Glu Val Gln Ser Leu Asp Ser Asp Ile Thr Ser Trp
        35                  40                  45

Asn Gly Gln Leu Leu Thr Ala Leu Pro Leu Leu Thr Asp Val Asp Thr
    50                  55                  60

Leu Glu Thr Asp Ile Lys Thr Ala Thr Thr Asp Thr Asn Asn Ser Ala
65                  70                  75                  80

Ala Phe Gly Asp Ala Asp Ser Ala Ser Ile Ala Ser Glu Thr Gln Ser
                85                  90                  95

Leu Ser Thr Leu Ile Val Thr Thr Leu Asp Asp Leu Val Ala Gln Ala
            100                 105                 110

Ser Lys Val Ala Ala Val Gly Leu Thr Ser Thr Val Glu Ser Ser Leu
        115                 120                 125

Glu Asp Leu Lys Thr Leu Ser Asp Gly Leu Ile Ser Ala Leu Glu Ser
    130                 135                 140

Lys Ile Glu Ala Ser Tyr Leu Pro Thr Ala Thr Ser Ile Ala Ala Ala
145                 150                 155                 160

Ile Asp Ser Ala Phe Ala Thr Ala Ile Ala Ala Tyr Ala
                165                 170

<210> SEQ ID NO 8
<211> LENGTH: 395
<212> TYPE: PRT
<213> ORGANISM: Penicillium funiculosum

<400> SEQUENCE: 8

Met Arg Ser Thr Ser Thr Phe Val Ala Ser Ala Ile Leu Ala Val Ala
1               5                   10                  15

Ser Val Gln Ala Gln Gln Thr Gly Tyr Gly Gln Cys Gly Gly Glu Asn
            20                  25                  30

Trp Thr Gly Ala Thr Thr Cys Val Ser Gly Trp Thr Cys Thr Tyr Leu
        35                  40                  45

Asn Asp Trp Tyr Ser Gln Cys Leu Pro Ala Ser Ser Thr Leu Thr Thr
    50                  55                  60

Thr Thr Ser Ser Lys Thr Ser Thr Ala Thr Thr Ser Lys Thr
65                  70                  75                  80

Thr Thr Ser Ser Thr Ser Ser Pro Thr Ser Thr Gly Lys Leu Lys Trp
                85                  90                  95

Phe Gly Val Asp Glu Ser Cys Ala Glu Phe Gly Thr Ala Met Pro Gly
            100                 105                 110

Thr Trp Gly Val Asp Phe Thr Phe Ala Asn Thr Ala Thr Ile Gly Glu
        115                 120                 125

Phe Ile Ser Gln Gly Phe Asn Ile Phe Arg Ile Pro Phe Ala Met Glu
    130                 135                 140

Arg Met Val Gln Gly Ser Ile Asp Ala Ala Leu Asn Thr Ala Tyr Leu
145                 150                 155                 160

Thr Asn Tyr Ser Val Ala Val Asn Tyr Ile Thr Ser Asn Gly Ala Tyr
                165                 170                 175
```

Ala Val Ile Asp Pro His Asn Tyr Gly Arg Tyr Asn Gly Ser Ile Ile
                180                 185                 190

Thr Asp Thr Thr Ala Phe Gln Thr Phe Trp Ser Asn Leu Ala Thr Ala
            195                 200                 205

Phe Lys Ser Asn Ser Lys Val Ile Phe Asp Thr Asn Glu Tyr His
210                 215                 220

Asp Met Asp Glu Thr Leu Val Phe Asn Leu Asn Gln Ala Ala Ile Asp
225                 230                 235                 240

Gly Ile Arg Gly Ala Gly Ala Thr Thr Gln Tyr Ile Phe Ala Glu Gly
                245                 250                 255

Asn Ser Trp Thr Gly Ala Trp Thr Trp Asn Thr Thr Asn Asp Ser Leu
                260                 265                 270

Lys Asp Leu Ser Asp Pro Glu Asn Leu Leu Val Tyr Glu Met His Gln
                275                 280                 285

Tyr Leu Asp Ser Asp Gly Ser Gly Thr Asn Ser Ala Cys Val Ser Ser
                290                 295                 300

Thr Ile Gly Val Glu Arg Val Glu Gly Ala Thr Ala Trp Leu Gln Ala
305                 310                 315                 320

Asn Lys Lys Leu Gly Val Leu Gly Glu Tyr Ala Gly Gly Pro Asn Ser
                325                 330                 335

Val Cys Gln Ala Ala Val Thr Gly Met Leu Asp His Leu Val Ala Asn
                340                 345                 350

Asn Asp Val Trp Leu Gly Ala Ile Phe Trp Ser Ala Gly Pro Trp Trp
                355                 360                 365

Pro Gln Ser Thr Trp Ser Asn Met Glu Pro Pro Asn Gly Gln Ala Tyr
                370                 375                 380

Val Tyr Tyr Asp Asp Ile Leu Arg Ala Tyr Thr
385                 390                 395

<210> SEQ ID NO 9
<211> LENGTH: 310
<212> TYPE: PRT
<213> ORGANISM: Penicillium funiculosum

<400> SEQUENCE: 9

Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
                20                  25                  30

Lys Ser Tyr Ser Gly Tyr Leu Val Asn Gln Phe Pro Tyr Glu Ser Asn
                35                  40                  45

Pro Pro Ala Val Ile Gly Trp Ala Thr Thr Ala Thr Asp Leu Gly Phe
50                  55                  60

Val Ala Pro Ser Glu Tyr Thr Asn Ala Asp Ile Ile Cys His Lys Asn
65                  70                  75                  80

Ala Thr Pro Gly Ala Leu Ser Pro Val Ala Gly Gly Thr Val
                85                  90                  95

Glu Leu Gln Trp Thr Thr Trp Pro Asp Ser His His Gly Pro Val Ile
                100                 105                 110

Ser Tyr Leu Ala Asn Cys Asn Gly Asn Cys Ser Thr Val Asp Lys Thr
                115                 120                 125

Lys Leu Asn Phe Val Lys Ile Asp Gln Gly Gly Leu Ile Asp Asp Thr
                130                 135                 140

Thr Pro Pro Gly Thr Trp Ala Ser Asp Lys Leu Ile Ala Ala Asn Asn

```
            145                 150                 155                 160
Ser Trp Thr Val Thr Ile Pro Ser Thr Ile Ala Pro Gly Asn Tyr Val
                    165                 170                 175

Leu Arg His Glu Ile Ile Ala Leu His Ser Ala Gly Asn Ala Asp Gly
                180                 185                 190

Ala Gln Asn Tyr Pro Gln Cys Ile Asn Leu Glu Ile Thr Gly Ser Gly
                195                 200                 205

Thr Ala Ala Pro Ser Gly Thr Ala Gly Glu Lys Leu Tyr Thr Ser Thr
            210                 215                 220

Asp Pro Gly Ile Leu Val Asn Ile Tyr Gln Ser Leu Ser Thr Tyr Val
225                 230                 235                 240

Ile Pro Gly Pro Thr Leu Trp Ser Gly Ala Ala Asn Gly Ala Ala Ala
                245                 250                 255

Ala Ser Ala Thr Ala Thr Pro Thr Thr Leu Val Thr Ser Val Ala Pro
                260                 265                 270

Ala Ser Ser Thr Ser Ala Thr Ala Val Val Thr Thr Val Ala Pro Ala
                275                 280                 285

Val Thr Asp Val Val Thr Val Thr Asp Val Val Thr Val Thr Thr Val
            290                 295                 300

Ile Thr Thr Thr Val Leu
305                 310

<210> SEQ ID NO 10
<211> LENGTH: 464
<212> TYPE: PRT
<213> ORGANISM: Penicillium funiculosum

<400> SEQUENCE: 10

Met Leu Arg Tyr Leu Ser Ile Val Ala Ala Thr Ala Ile Leu Thr Gly
1               5                   10                  15

Val Glu Ala Gln Gln Ser Val Trp Gly Gln Cys Gly Gly Gln Gly Trp
                20                  25                  30

Ser Gly Ala Thr Ser Cys Ala Ala Gly Ser Thr Cys Ser Thr Leu Asn
            35                  40                  45

Pro Cys Lys Ala Asn Cys Ser Leu Asp Tyr Ala Gln Cys Ile Pro Gly
    50                  55                  60

Thr Ala Thr Ser Thr Thr Leu Val Lys Thr Thr Ser Ser Thr Ser Val
65                  70                  75                  80

Gly Thr Thr Ser Pro Pro Thr Thr Thr Thr Lys Ala Ser Thr Thr Thr
                85                  90                  95

Ala Thr Thr Thr Ala Ala Ala Ser Gly Asn Pro Phe Ser Gly Tyr Gln
                100                 105                 110

Leu Tyr Ala Asn Pro Tyr Tyr Ser Ser Glu Val His Thr Leu Ala Ile
            115                 120                 125

Pro Ser Leu Thr Gly Ser Leu Ala Ala Ala Thr Lys Ala Ala Glu
            130                 135                 140

Ile Pro Ser Phe Val Trp Leu Asp Thr Ala Ala Lys Val Pro Thr Met
145                 150                 155                 160

Gly Thr Tyr Leu Ala Asn Ile Glu Ala Ala Asn Lys Ala Gly Ala Ser
                165                 170                 175

Pro Pro Ile Ala Gly Ile Phe Val Val Tyr Asp Leu Pro Asp Arg Asp
            180                 185                 190

Cys Ala Ala Ala Ala Ser Asn Gly Glu Tyr Thr Val Ala Asn Asn Gly
            195                 200                 205
```

```
Val Ala Asn Tyr Lys Ala Tyr Ile Asp Ser Ile Val Ala Gln Leu Lys
    210                 215                 220

Ala Tyr Pro Asp Val His Thr Ile Leu Ile Glu Pro Asp Ser Leu
225                 230                 235                 240

Ala Asn Met Val Thr Asn Leu Ser Thr Ala Lys Cys Ala Glu Ala Gln
                245                 250                 255

Ser Ala Tyr Tyr Glu Cys Val Asn Tyr Ala Leu Ile Asn Leu Asn Leu
            260                 265                 270

Ala Asn Val Ala Met Tyr Ile Asp Ala Gly His Ala Gly Trp Leu Gly
        275                 280                 285

Trp Ser Ala Asn Leu Ser Pro Ala Ala Gln Leu Phe Ala Thr Val Tyr
    290                 295                 300

Lys Asn Ala Ser Ala Pro Ala Ser Leu Arg Gly Leu Ala Thr Asn Val
305                 310                 315                 320

Ala Asn Tyr Asn Ala Trp Ser Ile Ser Ser Pro Ser Tyr Thr Ser
                325                 330                 335

Gly Asp Ser Asn Tyr Asp Glu Lys Leu Tyr Ile Asn Ala Leu Ser Pro
            340                 345                 350

Leu Leu Thr Ser Asn Gly Trp Pro Asn Ala His Phe Ile Met Asp Thr
        355                 360                 365

Ser Arg Asn Gly Val Gln Pro Thr Lys Gln Gln Ala Trp Gly Asp Trp
    370                 375                 380

Cys Asn Val Ile Gly Thr Gly Phe Gly Val Gln Pro Thr Thr Asn Thr
385                 390                 395                 400

Gly Asp Pro Leu Glu Asp Ala Phe Val Trp Val Lys Pro Gly Gly Glu
                405                 410                 415

Ser Asp Gly Thr Ser Asn Ser Ser Ala Thr Arg Tyr Asp Phe His Cys
            420                 425                 430

Gly Tyr Ser Asp Ala Leu Gln Pro Ala Pro Glu Ala Gly Thr Trp Phe
        435                 440                 445

Gln Ala Tyr Phe Val Gln Leu Leu Thr Asn Ala Asn Pro Ala Leu Val
    450                 455                 460

<210> SEQ ID NO 11
<211> LENGTH: 251
<212> TYPE: PRT
<213> ORGANISM: Penicillium funiculosum

<400> SEQUENCE: 11

Met Lys Leu Gly Tyr Leu Ala His Leu Pro Ala Leu Val Gly Thr Ala
1               5                   10                  15

Cys Ala Tyr Leu Ala Thr Thr Arg Tyr Tyr Asp Gly Gln Glu Gly
            20                  25                  30

Ala Cys Gly Cys Gly Thr Ser Ser Gly Ile Asp Ser Trp Gln Leu Gly
        35                  40                  45

Ile Ser Ser Gly Val Tyr Thr Ala Ala Gly Ser Gln Ala Phe Phe Asp
    50                  55                  60

Thr Ala Gly Ala Thr Trp Cys Gly Ala Gly Cys Gly Lys Cys Tyr Asn
65                  70                  75                  80

Leu Thr Ser Thr Gly Ser Ser Pro Cys Asn Gly Cys Gly Leu Gly Gly
                85                  90                  95

Val Ala Gly Glu Ser Ile Ile Val Met Val Thr Asn Leu Cys Pro Tyr
            100                 105                 110

Asn Gly Asn Gln Gln Trp Cys Pro Gln Val Gly Gly Thr Asn Gln Tyr
        115                 120                 125
```

```
Gly Tyr Ser Tyr His Phe Asp Ile Met Ala Gln Ser Glu Ile Phe Gly
            130                 135                 140

Asp Asn Val Val Val Asn Phe Glu Pro Val Ala Cys Pro Gly Gln Ala
145                 150                 155                 160

Thr Ser Asp Trp Glu Thr Cys Val Cys Tyr Gly Glu Thr Ala Thr Asp
                165                 170                 175

Val Thr Pro Val Gly Leu Thr Ser Gly Gly Ser Ser Ser Ser Ser Ser
            180                 185                 190

Ser Thr Ser Pro Thr Gln Thr Thr Thr Arg Thr Ser Thr Ser Thr
        195                 200                 205

Ser Ser Ser Ala Gly Ala Thr Gln Thr Val Tyr Gly Gln Cys Gly Gly
            210                 215                 220

Ser Gly Trp Thr Gly Ala Thr Thr Cys Ala Ala Gly Ser Thr Cys Lys
225                 230                 235                 240

Ala Glu Asn Gln Trp Tyr Ser Gln Cys Leu Pro
                245                 250

<210> SEQ ID NO 12
<211> LENGTH: 464
<212> TYPE: PRT
<213> ORGANISM: Penicillium funiculosum

<400> SEQUENCE: 12

Met Phe Pro Lys Ile Lys Pro Glu Arg Thr Ser Leu Phe Ala Leu Gly
1               5                   10                  15

Leu Leu Ala Ser Ser Ser Leu Val Thr Ala Thr Gly Pro Cys Asp Ile
            20                  25                  30

Tyr Ser Ser Gly Gly Thr Pro Cys Val Ala Ala His Ser Thr Thr Arg
        35                  40                  45

Ala Leu Tyr Ala Ser Tyr Ser Gly Ala Leu Tyr Gln Val Lys Arg Gly
    50                  55                  60

Ser Asp Gly Ala Thr Thr Thr Ile Ser Pro Leu Ser Ala Gly Gly Val
65                  70                  75                  80

Ala Asn Ala Ala Ala Gln Asp Thr Phe Cys Ala Asn Thr Thr Cys Leu
                85                  90                  95

Ile Thr Ile Ile Tyr Asp Gln Ser Gly Arg Gly Asn His Leu Thr Gln
            100                 105                 110

Ala Pro Pro Gly Gly Phe Asp Gly Pro Asp Val Asn Gly Tyr Asp Asn
        115                 120                 125

Leu Ala Gly Ala Ile Gly Ala Pro Val Thr Leu Asn Gly Gln Lys Ala
    130                 135                 140

Tyr Gly Val Phe Ile Ser Pro Gly Thr Gly Tyr Arg Asn Asn Ala Ala
145                 150                 155                 160

Ser Gly Thr Ala Thr Gly Asp Ala Ala Glu Gly Met Tyr Ala Val Leu
                165                 170                 175

Asp Gly Thr His Tyr Asn Gly Gln Cys Cys Phe Asp Tyr Gly Asn Ala
            180                 185                 190

Glu Thr Ser Ser Thr Asp Thr Gly Asn Gly His Met Glu Ala Ile Tyr
        195                 200                 205

Tyr Gly Asp Ala Thr Tyr Trp Gly Ser Gly Ser Gly Pro Trp
    210                 215                 220

Ile Met Ala Asp Leu Glu Asn Gly Leu Phe Ser Gly Glu Ser Thr Gly
225                 230                 235                 240

Val Asn Ser Ala Asp Pro Ser Leu Ser Tyr Arg Phe Val Thr Ala Val
```

```
            245                 250                 255
Val Lys Gly Glu Pro Asn Phe Trp Ala Ile Arg Gly Asn Ala Ala
        260                 265                 270

Ser Gly Ser Leu Ser Thr Tyr Tyr Ser Gly Val Arg Pro Gln Val Ser
        275                 280                 285

Gly Tyr Tyr Pro Met His Lys Glu Gly Ala Ile Ile Leu Gly Ile Gly
        290                 295                 300

Gly Asp Asn Ser Asn Val Thr Val Gly Ser Ala Ile Ser Leu His Val
305                 310                 315                 320

Thr Thr Ala Gly Tyr Thr Thr Arg Tyr Ile Ala His Asn Gly Thr Thr
                325                 330                 335

Val Asn Thr Gln Val Val Ser Ser Ser Thr Thr Leu Lys Glu
        340                 345                 350

Gln Ala Ser Trp Thr Val Arg Thr Gly Leu Gly Asn Ser Ala Cys Phe
        355                 360                 365

Ser Phe Glu Ser Val Asp Thr Pro Gly Ser Tyr Ile Arg His Tyr Asn
        370                 375                 380

Phe Glu Leu Leu Leu Asn Ala Asn Asp Gly Thr Lys Gln Phe Tyr Glu
385                 390                 395                 400

Asp Ala Thr Phe Cys Pro Gln Ser Gly Leu Ser Gly Thr Gly Thr Ser
                405                 410                 415

Leu Arg Ser Trp Ser Tyr Pro Thr Arg Tyr Phe Arg His Tyr Asn Asn
                420                 425                 430

Val Leu Tyr Ala Ala Ser Asn Gly Gly Val Gln Thr Phe Asp Ala Thr
                435                 440                 445

Ala Ser Phe Asn Ala Asp Val Thr Phe Leu Val Glu Thr Ala Phe Ala
        450                 455                 460

<210> SEQ ID NO 13
<211> LENGTH: 283
<212> TYPE: PRT
<213> ORGANISM: Penicillium funiculosum

<400> SEQUENCE: 13

Met Leu Ser Arg Ile Leu Gly Leu Ser Ala Leu Val Gly Gly Ala Leu
1               5                   10                  15

Ser Ile Pro Ile Glu Lys Arg Ala Cys Pro Asn Ile His Val Phe Gly
            20                  25                  30

Ala Arg Glu Thr Thr Val Ser Gln Gly Tyr Gly Ser Ser Ile Thr Val
        35                  40                  45

Val Asn Asp Val Leu Asn Ala Tyr Ser Gly Ser Thr Ala Glu Ala Ile
    50                  55                  60

Val Tyr Pro Ala Cys Gly Gly Gln Ser Ser Cys Gly Gly Val Ser Tyr
65                  70                  75                  80

Ser Ser Ser Val Ala Gln Gly Ile Ala Ala Val Ala Ser Ala Val Asn
                85                  90                  95

Ser Phe His Thr Glu Cys Pro Asn Thr Glu Ile Val Leu Val Gly Tyr
            100                 105                 110

Ser Gln Gly Gly Glu Ile Met Asp Val Ala Leu Cys Gly Gly Gly Asp
        115                 120                 125

Pro Asn Gln Gly Tyr Thr Asn Thr Ala Val Gln Leu Ser Ala Ser Ala
    130                 135                 140

Leu Ser Met Val Lys Ala Ala Ile Phe Met Gly Asp Pro Leu Phe Arg
145                 150                 155                 160
```

```
Ala Gly Leu Ser Tyr Glu Val Gly Thr Cys Thr Ala Gly Gly Phe Asp
            165                 170                 175

Glu Arg Pro Ala Gly Phe Ser Cys Pro Ser Ala Ser Leu Ile Gln Ser
        180                 185                 190

Tyr Cys Asp Ala Ser Asp Pro Tyr Cys Cys Asn Gly Ser Asn Ala Ala
            195                 200                 205

Thr His Gln Gly Tyr Gly Ala Glu Tyr Gly Asn Gln Ala Leu Ala Phe
        210                 215                 220

Ile Lys Ser Lys Leu Ser Gly Gly Thr Thr Ser Pro Gly Asn Gly
225                 230                 235                 240

Thr Thr Gly Thr Gly Gly Thr Val Ala Gln Trp Gly Gln Cys Gly
            245                 250                 255

Gly Leu Gly Trp Thr Gly Ala Thr Thr Cys Val Ser Pro Tyr Thr Cys
            260                 265                 270

Thr Val Ile Asn Ser Tyr Tyr Ser Gln Cys Leu
            275                 280
```

<210> SEQ ID NO 14
<211> LENGTH: 263
<212> TYPE: PRT
<213> ORGANISM: Penicillium funiculosum

<400> SEQUENCE: 14

```
Leu Val Leu Leu Gly Asp Ser Ile Thr Glu Ile Thr Cys Trp Arg Pro
1               5                   10                  15

Leu Val Trp Glu Gln Ile Thr Ser Ala Gly Leu Ala Gly Ser Val Asp
            20                  25                  30

Phe Val Gly Ser Met Asn Asp Leu Gln Pro Asn Cys Ser Arg Pro Gln
        35                  40                  45

Gly Phe Asp Pro Asp His Glu Gly His Ser Gly Trp Gln Ala Tyr Asp
    50                  55                  60

Ile Ala Arg Asn Asn Ile Ala Gly Trp Val Gln Asn Thr Lys Pro Asp
65                  70                  75                  80

Ile Val Gln Phe Met Leu Gly Thr Asn Asp Val Asn Ile Gly His Arg
                85                  90                  95

Asn Ala Asp Ser Ile Ile Gly Ser Tyr Thr Ile Met Leu Asn Ala Met
            100                 105                 110

Arg Ala Ala Asn Pro Arg Val Lys Val Ile Val Asp Lys Ile Ile Pro
        115                 120                 125

Thr Ser Trp Ser Asp Ala Thr Ile Glu Ala Val Asn Thr Ala Ile Pro
    130                 135                 140

Gly Trp Val Gln Gln Thr Thr Ala Glu Ser Pro Val Val Ile Ala
145                 150                 155                 160

Asp Cys Ser Arg Ala Ala Gly Phe Thr Asn Asp Met Leu Arg Asp Asp
                165                 170                 175

Gly Val His Pro Asn Ser Lys Gly Asp Gln Phe Ile Ala Gly Gln Ile
            180                 185                 190

Gly Pro Lys Leu Ile Gln Leu Ile Lys Asp Val Ser Thr Gly Thr Thr
        195                 200                 205

Ser Ser Thr Ser Thr Ser Ser Thr Ser Pro Thr Ser Thr Ser Gly Gly
    210                 215                 220

Ser Gly Thr Gly Ala Ala His Trp Gly Gln Cys Gly Gly Ile Gly Trp
225                 230                 235                 240

Asn Gly Ala Thr Thr Cys Val Ser Pro Tyr Thr Cys Gln Gln Val Asn
                245                 250                 255
```

Pro Tyr Tyr Tyr Gln Cys Leu
            260

<210> SEQ ID NO 15
<211> LENGTH: 313
<212> TYPE: PRT
<213> ORGANISM: Penicillium funiculosum

<400> SEQUENCE: 15

Met Leu His Asn Leu Ala Ser Pro Leu Ile Ala Leu Ala Leu Ser
1               5                   10                  15

Gln Ser Val Leu Ser Phe Pro Leu Thr Arg Arg Leu Asp Asn Gly Ala
            20                  25                  30

Pro Leu Arg Asn Val Gln Tyr Val Gln Thr Phe Thr Asp Pro Ser Gly
        35                  40                  45

Asn Trp Phe Asn Leu Thr Asp Leu Val Thr Gln Asn Thr Gly Leu Thr
    50                  55                  60

His Leu Ile Leu Ala Ser Leu His Leu Asp Asn Pro Thr Glu Ile His
65                  70                  75                  80

Leu Asn Asp Asn Asp Ile Glu Gly Pro Tyr Trp Asp Thr Leu Trp Pro
                85                  90                  95

Met Val Ser Ser Leu Gln Ala Ala Gly Val Lys Val Met Leu Met Met
            100                 105                 110

Gly Gly Ala Ala Arg Gly Ser Tyr Ala Asn Leu Gln Asn Asp Phe Asp
        115                 120                 125

Thr Tyr Tyr Pro Ile Ile Leu Ser Ile Leu Arg Asn His Asn Leu Asp
    130                 135                 140

Gly Phe Asp Met Asp Val Glu Glu Asn Val Ser Glu Ser Val Leu Leu
145                 150                 155                 160

Arg Leu Ala Gln Gln Leu Asp Ala Asp Met Gly Ser Asp Phe Ile Leu
                165                 170                 175

Thr Ala Ala Pro Val Ala Leu Ser Met Ser Asn Gly Gly Asn Leu Asp
            180                 185                 190

Asn Val Ser Trp Ser Ala Leu Asp Gln Val Ala Ile Ser Ser Asn Arg
        195                 200                 205

Pro Asn Gly Lys Leu Phe Asn Trp Tyr Asn Thr Gln Phe Tyr Asp Gly
    210                 215                 220

Trp Gly Thr Ala Ala Ser Thr Thr Ser Tyr Asp Ser Ile Ile Ser Ala
225                 230                 235                 240

Gly Trp Asp Pro Ser Arg Ile Val Leu Gly Val Leu Thr Ala Ala Ser
                245                 250                 255

Ala Gly Tyr Ser Trp Gln Pro Thr Ser Val Leu Ser Thr Thr Ile Ala
            260                 265                 270

Ser Leu Lys Ala Lys Tyr Ala Asn Phe Gly Gly Val Phe Gly Trp Glu
        275                 280                 285

Tyr Gly Leu Ala Gly Glu Ser Asp Gly Gln Thr Pro Val Glu Trp Val
    290                 295                 300

Gly Ser Ile Gly Arg Tyr Leu Ala Ala
305                 310

<210> SEQ ID NO 16
<211> LENGTH: 626
<212> TYPE: PRT
<213> ORGANISM: Penicillium funiculosum

<400> SEQUENCE: 16

```
Met Thr Phe Ser Arg Leu Ser Ser Leu Leu Cys Ala Leu Ala Ala Phe
1               5                   10                  15

Gly His Ser Ala Leu Gly Ala Pro Gly Leu Phe Pro Arg Ala Thr Thr
            20                  25                  30

Ser Leu Asp Ala Trp Leu Ala Ser Glu Thr Thr Val Ser Leu Asn Gly
            35                  40                  45

Ile Leu Asp Asn Ile Gly Ala Ser Gly Ala Tyr Ala Ala Ser Ala Lys
    50                  55                  60

Ala Gly Val Val Ile Ala Ser Pro Ser Thr Ser Asn Pro Asp Tyr Tyr
65                      70                  75                  80

Tyr Thr Trp Thr Arg Asp Ser Ala Leu Thr Leu Lys Val Leu Ile Asp
                85                  90                  95

Leu Phe Arg Asn Gly Asn Leu Ser Leu Gln Thr Ile Ile Glu Glu Tyr
                100                 105                 110

Val Asn Ala Gln Ala Tyr Leu Gln Thr Val Ser Asn Pro Ser Gly Asp
            115                 120                 125

Leu Ser Ser Gly Leu Gly Leu Ala Glu Pro Lys Phe Asn Val Asp Met
        130                 135                 140

Ser Ala Tyr Thr Gly Ser Trp Gly Arg Pro Gln Arg Asp Gly Pro Ala
145                 150                 155                 160

Leu Arg Ala Ile Ala Leu Ile Asp Phe Gly Asn Trp Leu Leu Asp Asn
                165                 170                 175

Gly Tyr Ser Ser Tyr Ala Ile Ser Asn Ile Trp Pro Ile Val Arg Asn
                180                 185                 190

Asp Leu Ser Tyr Val Ala Gln Tyr Trp Ser Gln Ser Gly Tyr Asp Leu
            195                 200                 205

Trp Glu Glu Val Asn Ser Met Ser Phe Phe Thr Val Ala Asn Gln His
210                 215                 220

Arg Ala Leu Val Glu Gly Ser Thr Phe Ala Gly Arg Val Gly Ala Ser
225                 230                 235                 240

Cys Ser Trp Cys Asp Ser Gln Ala Pro Gln Ile Leu Cys Tyr Met Gln
                245                 250                 255

Thr Phe Trp Thr Gly Ser Tyr Ile Asn Ala Asn Thr Gly Gly Gly Arg
            260                 265                 270

Ser Gly Lys Asp Ala Asn Thr Val Leu Leu Ala Ile Asn Thr Phe Asp
        275                 280                 285

Pro Glu Ala Thr Cys Asp Asp Val Thr Phe Gln Pro Cys Ser Pro Arg
    290                 295                 300

Ala Leu Ala Asn His Lys Val Tyr Thr Asp Ser Phe Arg Ser Val Tyr
305                 310                 315                 320

Ser Leu Asn Ser Gly Ile Ala Glu Gly Val Ala Val Ser Val Gly Arg
                325                 330                 335

Tyr Pro Glu Asp Ser Tyr Tyr Asn Gly Asn Pro Trp Phe Leu Thr Thr
            340                 345                 350

Thr Ala Ala Ala Glu Gln Leu Tyr Asp Ala Ile Tyr Gln Trp Asn Lys
        355                 360                 365

Ile Gly Ser Ile Thr Ile Thr Ser Thr Ser Leu Ala Phe Phe Gln Asp
    370                 375                 380

Val Tyr Ser Ser Ala Ala Val Gly Thr Tyr Ala Ser Gly Ser Thr Ala
385                 390                 395                 400

Phe Thr Ala Ile Ile Ser Ala Val Lys Thr Tyr Ala Asp Gly Tyr Met
                405                 410                 415
```

-continued

```
Ser Ile Ala Gln Thr His Ala Met Thr Asn Gly Ser Leu Ser Glu Gln
            420                 425                 430

Phe Asp Lys Ala Thr Gly Ser Glu Leu Ser Ala Arg Asp Leu Thr Trp
        435                 440                 445

Ser Tyr Ala Ala Leu Leu Thr Ala Asn Met Arg Arg Asn Gly Val Val
    450                 455                 460

Pro Pro Ser Trp Gly Ala Ala Ser Ala Asn Ser Val Pro Ser Ser Cys
465                 470                 475                 480

Ser Thr Gly Ser Ala Thr Gly Thr Tyr Ser Thr Pro Thr Gly Thr Ser
                485                 490                 495

Trp Pro Ser Thr Leu Thr Ser Gly Thr Ala Gly Gly Thr Thr Thr Thr
                500                 505                 510

Ser Thr Ser Thr Thr Ala Cys Thr Thr Pro Thr Ser Val Ala Val Thr
            515                 520                 525

Phe Asp Glu Ile Ala Thr Thr Thr Tyr Gly Glu Asn Val Phe Ile Val
        530                 535                 540

Gly Ser Ile Ser Gln Leu Gly Ser Trp Asn Thr Asn Asn Ala Ile Ala
545                 550                 555                 560

Leu Ser Ala Ser Lys Tyr Thr Ser Ser Asn Asn Leu Trp Tyr Ala Thr
                565                 570                 575

Ile Asn Leu Pro Ala Gly Thr Thr Phe Gln Tyr Lys Tyr Ile Arg Lys
            580                 585                 590

Glu Thr Asp Gly Thr Ile Lys Trp Glu Ser Asp Pro Asn Arg Ser Tyr
            595                 600                 605

Thr Val Pro Ser Gly Cys Gly Val Ser Thr Ala Thr Glu Asn Asp Thr
        610                 615                 620

Trp Arg
625
```

METHOD FOR OBTAINING A COMPOSITION FOR BIOMASS HYDROLYSIS

FIELD OF THE INVENTION

The present invention relates to the field of biotechnology. Particularly, the present invention relates to the field of proteomics. More particularly, the present invention relates to the field of biomass hydrolysis.

BACKGROUND OF THE INVENTION

The most abundant organic compound on earth is carbohydrates. The lignocellulosic biomass is composed of carbohydrate polymers—cellulose and hemicelluloses and an aromatic polymer, lignin. Bioconversion of this renewable lignocellulosic biomass generates sugar and fermentation of these sugars leads to the production of many commercially valuable end products such as biofuels.

There are two basic steps for the conversion of cellulose to ethanol, first is the hydrolysis of the cellulose molecules to sugars and second is the fermentation of these sugars to ethanol. Many microorganisms in nature, secretes enzymes that are able to hydrolyse cellulose.

The quest for cheaper and better enzymes needed for the efficient hydrolysis of lignocellulosic biomass has placed fungi in the limelight for bioprospecting research, either for the discovery of novel fungi and/or fungal enzymes. The efficiency of filamentous fungi as key players in carbon recycling in nature has placed them in the spotlight as potential sources of enzymes for converting recalcitrant lignocellulosic materials into precursors for industrial purposes. With an estimated 5.1 million species, they represent an unending pool for potential sources of cellulase producers with novel applications. The recent upward trend in the commercial launch of biorefineries that use lignocellulosic biomass as a source of sugars for advanced biofuel production is a testament. Several fungi have been reported with proven abilities to produce lignocellulosic enzymes; with the mutant strains of the fungus *Trichoderma reesei* dominating the industrial arena as the workhorse for the production of cellulases.

Recent insights about its genome however, have revealed an unexpectedly poor collection of genes and enzymes associated with biomass degradation when compared with other fungi having the ability to degrade biomass; underscoring the need to explore alternatives and/or complements. In addition, there are several reports of enzymes cocktails from different fungi outperforming enzyme preparations from *T. reesei* in the hydrolysis of biomass when applied at equal enzyme loadings, while some other reports complementary performance (synergism). However, the main obstacle in designing cost effective lignocellulolytic enzyme cocktail is the lack of knowledge on total enzyme inventory and exact molar concentration of each individual cellulolytic protein secreted by lignocellulose degrading microbial species. An understanding of the qualitative and quantitative composition of fungal secretome, the complex interactions of the various enzyme types and kinetic expression profiles will allow for the establishment of efficient in vitro lignocellulose utilization processes. Comprehending the enzymatic apparatus of cellulolytic strains, with a focus on achieving better efficiency thus, is a key biotechnological bottleneck to be overcome before the production of liquid biofuels from lignocellulosic biomass becomes a commercial reality.

In this regards, the mass spectrometric based proteomic analysis of the secretome serves as a valuable tool in the discovery of new enzymes or interesting enzyme complexes associated with improved lignocellulose deconstruction. While the advances in mass spectrometry based proteomics machines and methods continually aids in elucidating the biological roles of protein players in several biological process, it focuses more on the description of carbohydrate active proteins and accessory components involved in the degradation of plant cell wall polysaccharides in cellulolytic fungi.

EP1511848 discloses a method for degrading lignocellulose to sugars. This patent discloses Composition comprising novel enzyme mixtures that can be used directly on lignocelluloses substrate.

U.S. Pat. No. 8,318,461 discloses a process for the enzymatic hydrolysis of cellulose to produce a hydrolysis product comprising glucose from a pretreated lignocellulosic feedstock and enzymes for use in the process.

US20100273217 discloses a method for treating biomass. It discloses an enzyme mixture obtained from *Penicillium funiculosum*.

US20110250652 discloses a process which is based on the microbial production of enzymes from the growth of the fungus *Penicillium funiculosum* in a suitable culture medium with a cellulosic substrate.

There is a continuous need to search for new enzymes or enzyme mixtures, which enhance the efficiency of the degradation of the cellulosic biomass. Most of the fungi from the culture collection had been previously identified and designated as having potentials for the production of cellulases. However their classification had been based on the enzyme profiling and activity using cellulase mono components, but the performance on active biomass was hardly evaluated for majority of them. The present invention provides a strategy to incorporate the respective fungi performance on model substrates with observed activity on heterogeneous substrates and the secretome obtained from the most performing fungus of the present invention is analysed to get an in depth understanding of the enzymes sets secreted by the fungus, their abundance as well as their how they interact with each other to bring about effective biomass deconstruction.

OBJECT OF THE INVENTION

The object of the invention is to provide a composition for biomass hydrolysis.

SUMMARY OF THE INVENTION

The present invention discloses a composition for biomass hydrolysis. The components of the composition may be obtained by biological or synthetic means. Synthetically, the components of the composition of the present invention may be obtained by amino acid synthesis or may be procured commercially.

DETAILED DESCRIPTION OF THE INVENTION

Figure 1:
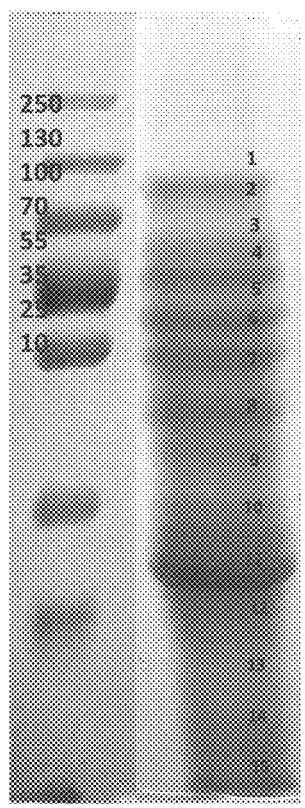
FIG. 1 depicts SDS-PAGE gel picture showing band position excised for LC-MS/MS.

The present invention provides a composition for hydrolysis of biomass comprising Cellobiohydrolase I (GH7-CBM1) in the range of 50%-75%, beta-D-glucoside glucohydrolase (GH3) in the range of 1%-4%, xylanase (GH11-CBM1) in the range of 1%-6%, swollenin in the range of 7%-13%, GMF family protein in the range of 1%-5%, IgE-binding protein in the range 1%-3%, Hydrophobic surface binding protein A in the range 1%-3%, endoglucanase (GH5-CBM1) in the range of 2%-25%, Lytic polysaccharide monooxygenases LPMO (AA9) in the range of 1%-5%.

The composition of the present invention optionally, comprises, cellobiohydrolase II (GH6-CBM1) in the range of 25%-40%, endoglucanase GH45 in the range of 0.50%-2.5%, alpha-L-arabinofuranosidase in the range of 2%-5%, acetyl xylan esterase (CE5-CBM1) in the range of (15%-30%), carbohydrate esterase (CE3-CBM1) in the range of 0.30%-2%, Glycoside Hydrolase family 18 protein (GH 18) in the range of 1%-4%, glucoamylase (GH15-CBM20) in the range of 8%-15%, The components of the composition of the present invention may be obtained by biological or synthetic sources; preferably the components of the present invention may be obtained from biological sources.

The components of the composition may be obtained from the biological source selected from the group comprising *Talaromyces* spp, *Acremonium* spp, *Penicillium* spp, preferably, *Penicillium* spp, more preferably *Penicillium funiculosum* (NCIM1228).

The method for obtaining the components of the composition of the present invention by biological means comprises the steps of:
a) collecting and selecting the potential cellulase degrading fungi;
b) culturing the fungi obtained in step (a) and obtaining the secretome;
c) selecting secretome based on enzyme activity;
d) selecting and ranking of secretome based on biomass hydrolyzing capabilities;
e) identifying preferred strains;
f) analysing secretome of the preferred strain;
g) obtaining/identifying the composition of the present invention The above steps (a tog) are described in detail below:
a) Collecting and Selecting the Potential Cellulase Degrading Fungi;

Potential cellulase degraders may be collected from actively decaying plant materials within the forested areas. The respective fungi may be isolated from the decaying plant materials using fungi culture media. The media used for culturing fungi of the present invention may be selected form the group comprising Brain-heart infusion agar, Czapek's agar, Inhibitory mold agar, Mycosel/Mycobiotic agar, Potato Dextrose Agar, Sabouraud's Heart Infusion agar, Sabouraud's dextrose agar, Potato flake agar and the like, more preferably Potato Dextrose Agar may be used. The plates may be then buried within the actively decaying plant materials and may be retrieved after few days. Actively growing fungi may be isolated from the retrieved plates in pure forms and may be subcultured on another culture media. The media for subculturing the fungi may be selected form the group comprising Brain-heart infusion agar, Czapek's agar, Inhibitory mold agar, Mycosel/Mycobiotic agar, Potato Dextrose Agar, Sabouraud's Heart Infusion agar, CMC-Trypan blue agar, Sabouraud's dextrose agar, Potato flake agar, and the like, preferably CMC-Trypan blue agar may be used. The biomass degrading potentials of the fungi strains may be evaluated based on the enzymatic index (EI) of the respective fungi. The enzymatic Index may be calculated as a function of the fungus growth (diameter) in relation to the diameter of the observed clear zones (halos) on agar media plate. Fungi exhibiting an enzymatic Index (EI) greater than or equal to one may be noted as potential biomass degraders.

b) Culturing the Fungi Obtained in Step (a) and Obtaining the Secretome

Fungi obtained from the different sources (step a) may be further cultivated in a cellulase inducing medium. Induced cultures may be centrifuged and supernatants may be filtered and the filtered secretome may be used for saccharification and enzyme assays.

c) Selecting Secretome Based on Enzyme Activity

The filtered secretome may be used for enzyme assay. The activities of enzymes towards carboxymethylcellulose (CMC), microcrystalline cellulose (Avicel PH-101) and Birchwood xylan, may be measured in buffer solution. The buffer solution used for the enzyme assay may be selected from the group comprising biocarbonate buffer solution, citrate-phosphate buffer, citric acictrisodium salt, HEPES sodium salt buffer solution and the like; preferably citrate-phosphate buffer may be used. The secretomes may comprise enzyme activity in the range of β-glucosidase (3.71±0.009 U/mg), endoglucanase (3.14±0.088 U/mg), cellobiohydrolase (0.20±0.019 U/mg), β-xylosidase (0.21±0.005 U/mg), endoxylanase (3.39±0.103 U/mg), polysaccharide monooxygenases (0.05±0.0003 U/mg) and filter paper activity (0.64±0.05 FPU/mg).

d) Selecting and Ranking of Secretome Based on Biomass Hydrolyzing Capabilities

The crude secretome obtained from the fungi may be evaluated for their biomass hydrolyzing capabilities. The biomass hydrolyzing potentials may be measured in buffer solution. The buffer solution used to measure biomass hydrolyzing potentials may be selected from the group comprising TRIS hydrochloride, biocarbonate buffer solution, citrate-phosphate buffer, citric acictrisodium salt, HEPES sodium salt buffer solution and the like, preferably citrate-phosphate buffer may be used. Sodium hydroxide and ammonia pre-treated wheat straw may be used as a substrate for the hydrolysis experiments. The main objective may be to identify fungi strains that secrete active biomass hydrolyzing cocktails in copious amounts. The biomass hydrolysing potential of the most performing fungal strain may be evaluated with respect to a commercial enzyme—Advanced enzyme formulation (AETL). The secretomes have biomass mass hydrolyzing capabilities in the range of 70% to 100% on ammonium hydroxide treated wheat straw and sodium hydroxide treated wheat straw.

e) Identifying Preferred Strains;

The respective fungi may be rated and ranked for their suitability as potential sources for biomass hydrolysing enzymes using the weighted sum model (WSM). Given a set of $$A_i^{WSM-score} = \sum_{j=1}^{n} w_j a_{ij},$$

for $i = 1, 2, 3, \ldots, m$.

Alternatives M and N criteria a weighted sum score ($A_i^{WSM-score}$) may be described as follows:

Where (AiWSM-score)=the WSM score of the best alternative, N=the number of criteria, $a_{ij}$=the actual value of the ith alternative in terms of the jth criterion, $w_j$=the weight of the importance of the jth criterion. Using the performance of the respective fungi enzymes on carboxymethylcellulose (CMC), microcrystalline cellulose (Avicel PH-101), p-nitrophenyl-β-D-glucopyranoside (pNPG) and the pre-treated wheat straws as criteria for evaluation; a relative weight (w) may be assigned to the respective criterion based on the Pearson Correlation coefficients between the criteria. The preferred strains may be identified by PCR using primers.

Genomic DNA may be extracted from fungal colony. Amplification of the ITS regions of nuclear ribosomal RNA gene may be achieved using primers ITS1 (5'-TCCGTAGGTGAACCTTGCGG-3') and ITS4 (5'-TCCTCCGCTTATTGATATGC-3') with the genomic DNA as template. After amplification, PCR products may be analysed and purified. The sequencing of the purified products may be carried out and nucleotide sequences obtained may be curated manually and final consensus sequence may be subjected to pair wise similarity search against multiple fungi databases.

f) Analysing Secretome of the Preferred Strain;

The total proteins obtained from most performing strains may be separated by SDS-PAGE. The proteins may be identified by LC-MS/MS analysis or Nano-LC chromatography.

In one aspect of the present invention, fungi with promising potentials for industrial production of biomass hydrolysing enzymes may be identified. With the screening strategy that incorporated their respective performance on i.e., ammonium and sodium hydroxide pre-treated wheat straw (See Table 3, a positive correlation between enzyme performance on ammonium hydroxide treated wheat straw and sodium hydroxide treated wheat straw biomass may be observed.

Using the various performances as inputs, a weighted sum score ($A_i^{WSM-score}$) may be generated for the respective fungi to model their performances on both ammonia and sodium hydroxide treated wheat straw. The weighted sum model (WSM) has been described as the best known and simplest multi-criteria decision making method for evaluating a number of alternatives in terms of a number of decision criteria. Secretome analysis, apart from being an excellent method to understand the biological mechanisms of lignocellulose degradation, is a valuable tool in the search for new enzymes or interesting enzyme complexes in the biofuels field. After identification, the proteins in the "most performing" secretome may be analysed.

g) Obtaining/Identifying the Composition of the Present Invention

After analysing the secretome from "most performing" strains, a composition for biomass hydrolysis may be obtained. The present invention provides a composition for hydrolysis of biomass comprising Cellobiohydrolase I (GH7-CBM1) in the range of 50%-75%, Glycoside Hydrolase family 18 protein (GH 18) in the range of 1%-4%, beta-D-glucoside glucohydrolase (GH3) in the range of 1%-4%, alpha-L-arabinofyranosidase in the range of 2%-5%, glucoamylase (GH15-CBM20) in the range of 8%-15%, swollenin in the range of 7%-13%, GMF family protein in the range of 1%-5%. Optionally, in addition, the composition may contain endoglucanase (GH5-CBM1) in the range of 2%-25%, cellobiohydrolase II (GH6-CBM1) in the range of 25%-40%, endoglucanase GH45 in the range of 0.50%-2.5%, acetyl xylan esterase (CES-CBM1) in the range of (15%-30%), xylanase (GH11-CBM1) in the range of 1%-6%, carbohydrate esterase (CE3-CBM1) in the range of 0.30%-2%.

In an embodiment of the present invention, the method for identifying the most performing strains and obtaining the components of the composition of the present invention in their secretome comprising the steps of:

a) collecting and selecting the potential cellulase degrading fungi;
b) culturing the fungi obtained in step (a) and obtaining the secretome;
c) selecting secretome based on enzyme activity;
d) selecting and ranking of secretome based on biomass hydrolyzing capabilities;
e) identifying preferred strains;
f) analysing secretome of the preferred strain;
g) obtaining/identifying the composition of the present invention The above steps (a to g) are described in detail below:

a) Collecting and Selecting the Potential Cellulase Degrading Fungi;

Potential cellulase degraders may be collected from actively decaying plant materials within the forested areas. The respective fungi may be isolated from the decaying plant materials using fungi culture media. The media used for culturing fungi of the present invention may be selected form the group comprising Brain-heart infusion agar, Czapek's agar, Inhibitory mold agar, Mycosel/Mycobiotic agar, Potato Dextrose Agar, Sabouraud's Heart Infusion agar, Sabouraud's dextrose agar, Potato flake agar and the like, more preferably Potato Dextrose Agar may be used. The plates may be then buried within the actively decaying plant materials and may be retrieved after few days. Actively growing fungi may be isolated from the retrieved plates in pure forms and may be subcultured on another culture media. The media for subculturing the fungi may be selected form the group comprising Brain-heart infusion agar, Czapek's agar, Inhibitory mold agar, Mycosel/Mycobiotic agar, Potato Dextrose Agar, Sabouraud's Heart Infusion agar, CMC-Trypan blue agar, Sabouraud's dextrose agar, Potato flake agar, and the like, preferably CMC-Trypan blue agar may be used. The biomass degrading potentials of the fungi strains may be evaluated based on the enzymatic index (EI) of the respective fungi. The enzymatic Index may be calculated as a function of the fungus growth (diameter) in relation to the diameter of the observed clear zones (halos) on agar media plate. Fungi exhibiting an enzymatic Index (EI) greater than or equal to one may be noted as potential biomass degraders.

b) Culturing the Fungi Obtained in Step (a) and Obtaining the Secretome

Fungi obtained from the different sources (step a) may be further cultivated in a cellulase inducing medium. Induced cultures may be centrifuged and supernatants may be filtered and the filtered secretome may be used for saccharification and enzyme assays.

c) Selecting Secretome Based on Enzyme Activity

The filtered secretome may be used for enzyme assay. The activities of enzymes towards carboxymethylcellulose (CMC), microcrystalline cellulose (Avicel PH-101) and Birchwood xylan, may be measured in buffer solution. The buffer solution used for the enzyme assay may be selected from the group comprising biocarbonate buffer solution, citrate-phosphate buffer, citric acictrisodium salt, HEPES sodium salt buffer solution and the like; preferably citrate-phosphate buffer may be used. The secretomes may comprise enzyme activity in the range of β-glucosidase (3.71±0.009 U/mg), endoglucanase (3.14±0.088 U/mg), cellobiohydrolase (0.20±0.019 U/mg), β-xylosidase (0.21±0.005 U/mg), endoxylanase (3.39±0.103 U/mg), polysaccharide monooxygenases (0.05±0.0003 U/mg) and filter paper activity (0.64±0.05 FPU/mg).

d) Selecting and Ranking of Secretome Based on Biomass Hydrolyzing Capabilities

The crude secretome obtained from the fungi may be evaluated for their biomass hydrolyzing capabilities. The biomass hydrolyzing potentials may be measured in buffer solution. The buffer solution used to measure biomass hydrolyzing potentials may be selected from the group comprising TRIS hydrochloride, biocarbonate buffer solution, citrate-phosphate buffer, citric acictrisodium salt, HEPES sodium salt buffer solution and the like, preferably citrate-phosphate buffer may be used. Sodium hydroxide and ammonia pre-treated wheat straw may be used as a substrate for the hydrolysis experiments. The main objective may be to identify fungi strains that secrete active biomass hydrolyzing cocktails in copious amounts. The biomass hydrolysing potential of the most performing fungal strain may be evaluated with respect to a commercial enzyme—Advanced enzyme formulation (AETL). The secretomes have biomass mass hydrolyzing capabilities in the range of 70% to 100% on ammonium hydroxide treated wheat straw and sodium hydroxide treated wheat straw.

e) Identifying Preferred Strains;

The respective fungi may be rated and ranked for their suitability as potential sources for biomass hydrolysing enzymes using the weighted sum model (WSM). Given a set of $$A_i^{WSM-score} = \sum_{j=1}^{n} w_j a_{ij},$$

for $i = 1, 2, 3, \ldots, m$.

Alternatives M and N criteria a weighted sum score ($A_i^{WSM\text{-}score}$) may be described as follows:

Where (AiWSM-score)=the WSM score of the best alternative, N=the number of criteria, $a_{ij}$=the actual value of the ith alternative in terms of the jth criterion, $w_j$=the weight of the importance of the jth criterion. Using the performance of the respective fungi enzymes on carboxymethylcellulose (CMC), microcrystalline cellulose (Avicel PH-101), p-nitrophenyl-β-D-glucopyranoside (pNPG) and the pre-treated wheat straws as criteria for evaluation; a relative weight (w) may be assigned to the respective criterion based on the Pearson Correlation coefficients between the criteria. The preferred strains may be identified by PCR using primers.

Genomic DNA may be extracted from fungal colony. Amplification of the ITS regions of nuclear ribosomal RNA gene may be achieved using primers ITS1 (5'-TCCGTAGGTGAACCTTGCGG-3') and ITS4 (5'-TCCTCCGCTTATTGATATGC-3') with the genomic DNA as template. After amplification, PCR products may be analysed and purified. The sequencing of the purified products may be carried out and nucleotide sequences obtained may be curated manually and final consensus sequence may be subjected to pair wise similarity search against multiple fungi databases.

f) Analysing Secretome of the Preferred Strain;

The total proteins obtained from most performing strains may be separated by SDS-PAGE. The proteins may be identified by LC-MS/MS analysis or Nano-LC chromatography.

In one aspect of the present invention, fungi with promising potentials for industrial production of biomass hydrolysing enzymes may be identified. With the screening strategy that incorporated their respective performance on i.e., ammonium and sodium hydroxide pre-treated wheat straw (see Table 3), a positive correlation between enzyme performance on ammonium hydroxide treated wheat straw and sodium hydroxide treated wheat straw biomass may be observed.

Using the various performances as inputs, a weighted sum score ($A_i^{WSM\text{-}score}$) may be generated for the respective fungi to model their performances on both ammonia and sodium hydroxide treated wheat straw. The weighted sum model (WSM) has been described as the best known and simplest multi-criteria decision making method for evaluating a number of alternatives in terms of a number of decision criteria. Secretome analysis, apart from being an excellent method to understand the biological mechanisms of lignocellulose degradation, is a valuable tool in the search for new enzymes or interesting enzyme complexes in the biofuels field. After identification, the proteins in the "most performing" secretome may be analysed.

g) Obtaining/Identifying the Composition of the Present Invention

After analysing the secretome from "most performing" strains, a composition for biomass hydrolysis may be obtained. The present invention provides a composition for hydrolysis of biomass comprising Cellobiohydrolase I (GH7-CBM1) in the range of 50%-75%, Glycoside Hydrolase family 18 protein (GH 18) in the range of 1%-4%, beta-D-glucoside glucohydrolase (GH3) in the range of 1%-4%, alpha-L-arabinofyranosidase in the range of 2%-5%, glucoamylase (GH15-CBM20) in the range of 8%-15%, swollenin in the range of 7%-13%, GMF family protein in the range of 1%-5%. Optionally, in addition, the composition may contain endoglucanase (GH5-CBM1) in the range of 2%-25%, cellobiohydrolase II (GH6-CBM1) in the range of 25%-40%, endoglucanase GH45 in the range of 0.50%-2.5%, acetyl xylan esterase (CES-CBM1) in the range of (15%-30%), xylanase (GH11-CBM1) in the range of 1%-6%, carbohydrate esterase (CE3-CBM1) in the range of 0.30%-2%.

The present invention is illustrated herein by means of examples. The examples are intended for illustration only, and are not limiting with respect to the scope of the present invention.

EXAMPLES

Example-1: Collection and Identification of Potential Cellulase Degrading Fungi

The respective fungi were isolated from the decaying plant materials using potato dextrose agar plates to which 0.5% Avicel, 0.01% trypan blue and chloramphenicol 100 μm/mL were incorporated. The plates were buried within the actively decaying plant materials and retrieved after 4 days. Actively growing fungi were isolated from the retrieved plates in pure forms and subcultured on CMC-Trypan blue agar plates containing soya peptone (24 g/L), KH$_2$PO4 (5.9 g/L), (NH$_4$)$_2$SO4 (3.12 g/L), CaCl$_2$.2H$_2$O (0.05 g/L), yeast extract (0.05 g/L), Agar (15 g/L), Triton X-100 (0.01% v/v), trypan blue (0.01% w/v) and carboxymethyl cellulose (0.5% w/v). The pH was adjusted to 5.5. The biomass degrading potentials of the strains were evaluated after 5 days incubation at 28° C. based on the enzymatic index (EI) of the respective fungi. The enzymatic Index was calculated as a function of the fungus growth (diameter) in relation to the diameter of the observed clear zones (halos) on CMC-Trypan blue agar plate. Fungi exhibiting an enzymatic Index (EI) greater than or equal to one were noted as potential biomass degraders. Fungi obtained from National Collection of Industrial Microorganisms (NCIM), Pune—India were maintained on potato dextrose agar (PDA) and evaluated for its biomass degrading potentials. The list of all collected fungi is shown in Table 1.

TABLE 1

List of the fungi strains used in the study

| Laboratory Code | Name | Phylum | Family | Source | Culture collection number | ITS verification |
|---|---|---|---|---|---|---|
| L1 | Aspergillus niger | Ascomycota | Trichocomaceae | NCIM | 616 | Y |
| L2 | Neurospora crassa | Ascomycota | Sordariaceae | NCIM | 870 | N |
| L3 | Cladosporium sp. | Ascomycota | Davidiellaceae | NCIM | 901 | N |
| L4 | Aspergillus fumigatus | Ascomycota | Trichocomaceae | NCIM | 902 | N |

TABLE 1-continued

List of the fungi strains used in the study

| Laboratory Code | Name | Phylum | Family | Source | Culture collection number | ITS verification |
|---|---|---|---|---|---|---|
| L5 | *Myrothecium verrucaria* | Ascomycota | Incertae sedis | NCIM | 903 | N |
| L6 | *Myrothecium verrucaria* | Ascomycota | Incertae sedis | NCIM | 990 | N |
| L7 | *Neurospora crassa* | Ascomycota | Sordariaceae | NCIM | 1017 | N |
| L8 | *Neurospora crassa* | Ascomycota | Sordariaceae | NCIM | 1021 | Y |
| L9 | *Trichoderma reesei* | Ascomycota | Hypocreaceae | NCIM | 1052 | N |
| L10 | *Ptychogaster* sp. | Basidiomycota | Fomitopsidaceae | NCIM | 1074 | N |
| L11 | *Fusarium* sp. | Ascomycota | Nectriaceae | NCIM | 1075 | N |
| L12 | *Coriolus versicolor* | Basidiomycota | Polyporaceae | NCIM | 1076 | N |
| L13 | *Paecilomyces* sp. | Ascomycota | Trichocomaceae | NCIM | 1081 | N |
| L14 | *Sclerotium rolfsii* | Basidiomycota | Atheliaceae | NCIM | 1084 | N |
| L15 | *Pleurotus sajor-caju* | Basidiomycota | Polyporaceae | NCIM | 1133 | N |
| L16 | *Penicillium janthinellum* | Ascomycota | Trichocomaceae | NCIM | 1169 | N |
| L17 | *Penicillium janthinellum* | Ascomycota | Trichocomaceae | NCIM | 1171 | N |
| L18 | *Trichoderma viride* | Ascomycota | Hypocreaceae | NCIM | 1195 | N |
| L19 | *Phanerochaete chrysosporium* | Basidiomycota | Phanerochaetaceae | NCIM | 1197 | N |
| L20 | *Pleurotus ostreatus* | Basidiomycota | Pleurotaceae | NCIM | 1200 | N |
| L21 | *Trametes hirsuta* | Basidiomycota | Polyporaceae | NCIM | 1201 | Y |
| L22 | *Aspergillus terreus* | Ascomycota | Trichocomaceae | NCIM | 1202 | N |
| L23 | *Aspergillus awamori* | Ascomycota | Trichocomaceae | NCIM | 1225 | Y |
| L24 | *Aspergillus niger* | Ascomycota | Trichocomaceae | NCIM | 596A | N |
| L25 | *Aspergillus niger* | Ascomycota | Trichocomaceae | ICGEB | N/A | Y |
| L26 | *Aspergillus flavus* | Ascomycota | Trichocomaceae | ICGEB | N/A | Y |
| L27 | *Aspergillus flavus* | Ascomycota | Trichocomaceae | ICGEB | N/A | N |
| L28 | *Aspergillus flavipes* | Ascomycota | Trichocomaceae | ICGEB | N/A | Y |
| L29 | *Aspergillus* sp. | Ascomycota | Trichocomaceae | ICGEB | N/A | Y |
| L30 | *Aspergillus* sp. | Ascomycota | Trichocomaceae | ICGEB | N/A | Y |
| L31 | *Aspergillus* sp. | Ascomycota | Trichocomaceae | ICGEB | N/A | Y |
| L32 | *Penicillium* sp. | Ascomycota | Trichocomaceae | ICGEB | N/A | Y |
| L33 | *Aspergillus oryzae* strain FH4 | Ascomycota | Trichocomaceae | ICGEB | N/A | Y |
| L34 | *Aspergillus* sp | Ascomycota | Trichocomaceae | ICGEB | N/A | Y |
| L35 | *Aspergillus* sp. | Ascomycota | Trichocomaceae | ICGEB | N/A | Y |
| L36 | *Aspergillus niger* | Ascomycota | Trichocomaceae | ICGEB | N/A | Y |
| L37 | *Penicillium oxalicum* | Ascomycota | Trichocomaceae | ICGEB | N/A | Y |
| L38 | *Aspergillus* sp. | Ascomycota | Trichocomaceae | ICGEB | N/A | Y |
| L39 | *Penicillium citrinum* | Ascomycota | Trichocomaceae | ICGEB | N/A | Y |
| L40 | *Aspergillus* sp. | Ascomycota | Trichocomaceae | ICGEB | N/A | Y |
| L41 | *Trichoderma atroviride* | Ascomycota | Hypocreaceae | ICGEB | N/A | Y |
| L42 | *Penicillium funiculosum* | Ascomycota | Trichocomaceae | NCIM | 1228 | Y |
| L43 | *Trichoderma reesei* | Ascomycota | Hypocreaceae | NCIM | 992 | Y |
| L44 | *Trichoderma reesei* | Ascomycota | Hypocreaceae | NCIM | 1186 | Y |
| L45 | *Aspergillus niger* | Ascomycota | Trichocomaceae | ICGEB | N/A | N |

The fungi were screened for their respective performance on model substrates, i.e., CMC, pNPG and Avicel, as well as heterogeneous substrates, i.e., ammonium and sodium hydroxide pre-treated wheat straw. A positive correlation between enzyme performance on model substrates and biomass was observed (Table 2).

TABLE 2

Correlations Coefficients between Core Cellulases Activities and Actual Enzyme Performance on Pre-Treated Wheat Straw

|     | Endoglucanase | Exoglucanase | β-glucosidase |
| --- | --- | --- | --- |
| AMM | 0.55 | 0.92 | 0.47 |
| ALK | 0.75 | 0.90 | 0.53 |

Note:
$p < 0.05$
AMM = Ammonia pre-treated wheat straw
ALK = sodium hydroxide pre-treated wheat straw.

Example-2: Culture Conditions and Supernatant Preparation

Fungi obtained from the different sources were further cultivated in a cellulase inducing medium containing soya peptone (24 g/L), $KH_2PO_4$ (5.9 g/L), $(NH_4)_2SO_4$ (3.12 g/L), $CaCl_2 \cdot 2H_2O$ (0.05 g/L), yeast extract (0.05 g/L), wheat bran (24 g/L) and Avicel (21.4 g/L); the final pH was adjusted to 5.5. The cellulase inducing medium in Erlenmeyer flasks were inoculated with four plugs (1 mm diameter) from the edge of the actively growing fungi respectively. The flasks were kept at 30° C. for 6 days with orbital shaking at 150. Induced cultures were centrifuged at 7,000 rpm for 10 min at 4° C.; then, supernatants were filtered using syringe filters with a 0.45-μm PVDF membrane. For screening experiments, the filtered secretome were used for saccharification and enzyme assays. However, for subsequent evaluation of most performing secretome and proteomics experiments, the obtained secretome were concentrated using Vivaspin columns with a 5 kDa MWCO; then, culture media were replaced by citrate-phosphate buffer 50 mM, pH 5. The protein concentrations of the obtained secretome were determined by the Bicinchoninic acid (BCA) method using bovine serum albumin as a standard.

Example-3: Evaluating Enzyme Activity

All enzymatic activities were measured in citrate-phosphate buffer (50 mM, pH 5.0) and at 50° C. The activities of enzymes towards carboxymethylcellulose (CMC), microcrystalline cellulose (Avicel PH-101) and Birchwood xylan, were measured by using the dinitrosalicylic acid (DNSA) method. Briefly, 30 μL of crude secretome were mixed with 100 μL of substrates at 1% concentration and incubated for 30 minutes. The reaction was terminated by the addition of DNSA reagent and boiled for 10 min. The absorbance at 540 nm was measured relative to a glucose standard curve. One unit of enzyme activity was defined as the amount of protein that released 1 μmol of reducing sugar per min. β-glucosidase and β-xylosidase, activities were assayed by monitoring the release of p-nitrophenol from p-nitrophenyl-β-D-glucopyranoside (pNPG) and p-nitrophenyl-β-D-xylopyranoside (pNPX) respectively. Briefly, 30 μL of enzymes were mixed with 100 μL of substrate (1 mM) and incubated for 20 min. The reaction was stopped by adding 130 μL of 1 M sodium carbonate (pH 11.5), and the release of 4-nitrophenol was quantified at 410 nm using a 4-nitrophenol standard curve. One unit of enzyme activity was defined as the amount of protein that released 1 μmol of p-nitrophenol per min. Lytic polysaccharide monooxygenases (LPMOs) activity were assayed as follows—the reactions were performed in 100 mM sodium phosphate buffer, pH 6.0 at 22° C. The reaction mixture comprised of 20 μL dilutions of LPMO source (enzyme) and 180 μL assay solution which comprised 18 μL of 300 μM ascorbate, 18 μL of 500 μM Amplex Red, 18 μL of 71.4 units/ml HRP, 18 μL of 1 M sodium phosphate buffer pH 6.0 and 108 μL HPLC grade water. Resorufin fluorescence was taken at excitation wavelength of 530 nm and emission wavelength 580 nm after 10 minutes incubation using a multimode plate reader. In reference experiments without LPMO the background signal was measured and subtracted from the assays. A standard curve obtained with various dilutions of $H_2O_2$ was used for the calculation of an enzyme factor to convert the fluorimeter readout (counts min-1), into enzyme activity. LPMO activity is defined as one μmol $H_2O_2$ generated per minute under the defined assay conditions. Overall cellulase activity was determined using filter paper. Rolled Whatman No. 1 filter paper strip (1.0×6.0 cm) were incubated with the appropriate enzyme solutions for 1 hour at 50° C. The reducing sugars released were measured using the dinitrosalicylic acid method with glucose as the standard. One unit of filter paper activity was defined as the amount of protein that released 1 μmol of reducing sugar per min.

Example-4: Evaluating the Crude Secretome Obtained from the Fungi for their Biomass Hydrolyzing Capabilities—Saccharification Assays The biomass hydrolyzing potentials were measured in citrate-phosphate buffer (50 mM, pH 5.0) and at 50° C. with orbital shaking at 150 rpm. Wheat straw that had been subjected to sodium hydroxide and ammonia pre-treatment were used as substrates for the hydrolysis experiments respectively. The pre-treated straws were graded through a 0.5 mm mesh and stored at 4° C. Enzymatic hydrolysis were carried out in 1.2 mL capacity 96-wells deep ell plates sealed with adhesive PCR Plate Seals to prevent evaporation. The reaction mixture included the pre-treated wheat straws at 5% dry weight loading in a 250 μL final reaction volume containing the appropriate enzyme dilutions of the enzymes. The hydrolysis was carried out for 6 hours. Control experiments were carried out under the same conditions using substrates without enzymes (enzyme blank) and enzymes without substrates (substrate blank)—a substrate-free negative control was set up by filling wells with 50 mM citrate-phosphate buffer, pH 4.8, and the background of soluble sugars present in the wheat straw sample was determined by incubating wheat straw in the absence of enzyme. All assays were carried out in triplicate. The concentration of reducing sugars in the hydrolysates was analysed with the dinitrosalicylic acid method using glucose as a standard. The biomass hydrolysing potential of the most performing fungal strain was evaluated with respect to a commercial enzyme—Advanced enzyme formulation (AETL) (India). The conditions were as described above except that enzyme loading was normalized based on filter paper units (FPU) and the hydrolysis allowed for 36 hours with the concentration of reducing sugar in the hydrolysate determined at the interval of every 6 hour.

Example-5: Molecular Identification of Cellulase Positive Strains

Genomic DNA was extracted from 5-7 day old fungal colony grown on PDA plates and stored at −20° C. PCR was performed using standard procedures. In brief, amplification of the ITS regions of nuclear ribosomal RNA gene was achieved using primers ITS1 (5'-TCCGTAGGTGAACCT-TGCGG-3') and ITS4 (5'-TCCTCCGCTTATTGATATGC-3') with the genomic DNA as template. The corresponding ITS region was amplified from approximately 50 ng genomic DNA in 50 µL PCR reaction containing 200 nM primers, 200 nM dNTPs and 1 U Phusion® High-Fidelity. The PCR reaction was carried out using 30 cycles of denaturation at 98° C. for 15 seconds, annealing at 57° C. for 30 seconds, and extension at 72° C. for 25 seconds, with a final extension step at 72° C. for 2 minutes. PCR products were analysed by electrophoresis in 1% (w/v) agarose gels at 80V. The PCR products were purified using the Nucleo-Spin® Gel and PCR Clean-up kit. The sequencing of the purified products was carried out with a high throughput Applied Biosystems 3730XL Sequencers. The nucleotide sequences obtained were curated manually and final consensus sequence was subjected to pair wise similarity search against multiple fungi databases through the BioloMICS software.

Example-6: Identifying the *Penicillium funiculosum* (NCIM1228) as a Fungus with Promising Potentials for Biomass Hydrolysis The fungus *Penicillium funiculosum* ranked highest with an average weighted sum score of 59.80 (Table 3).

TABLE 3

Scoring of Strain Performance (Hydrolysis Potential) Using the Weighted Sum Model (Wsm)

| Identity | Name | Sum of weights for ALK | Sum of weights for AFEX | Average sum of weights |
|---|---|---|---|---|
| L1 | Aspergillus niger | 17.64 | 11.22 | 14.43 |
| L2 | Neurosporacrassa | 29.35 | 20.20 | 24.77 |
| L3 | Cladosporium sp. | 5.73 | 4.73 | 5.23 |
| L4 | Aspergillus fumigates | 5.56 | 5.45 | 5.51 |
| L5 | Myrothecium verrucaria | 5.60 | 5.43 | 5.51 |
| L6 | Myrothecium verrucaria | 6.03 | 5.65 | 5.84 |
| L7 | Neurosporacrassa | 6.91 | 6.28 | 6.60 |
| L8 | Neurosporacrassa | 33.64 | 19.28 | 26.46 |
| L9 | Trichoderma reesei | 5.77 | 5.23 | 5.50 |
| L10 | Ptychogaster sp. | 12.07 | 9.51 | 10.79 |
| L11 | Fusarium sp. | 5.57 | 5.24 | 5.40 |
| L12 | Coriolus versicolor | 30.84 | 22.39 | 26.62 |
| L13 | Paecilomyces sp. | 5.26 | 5.31 | 5.28 |
| L14 | Sclerotiumrolfsii | 5.75 | 5.32 | 5.54 |
| L15 | Pleurotussajor-caju | 5.58 | 5.43 | 5.50 |
| L16 | Penicillium janthinellum | 5.26 | 5.77 | 5.51 |
| L17 | Penicillium janthinellum | 5.42 | 5.13 | 5.27 |
| L18 | Trichoderma viride | 7.02 | 6.12 | 6.57 |
| L19 | Phanerochaetechrysosporium | 6.46 | 6.05 | 6.25 |
| L20 | Pleurotusostreatus | 8.39 | 5.99 | 7.19 |
| L21 | Trameteshirsute | 14.12 | 10.05 | 12.08 |
| L22 | Aspergillus terreus | 7.22 | 6.64 | 6.93 |
| L23 | Aspergillus awamori (niger) | 9.82 | 8.47 | 9.14 |
| L24 | Aspergillus niger | 7.03 | 6.34 | 6.69 |
| L25 | Aspergillus niger | 9.20 | 7.44 | 8.32 |
| L26 | Aspergillus flavus | 12.47 | 9.19 | 10.83 |
| L27 | Aspergillus flavus | 12.68 | 9.52 | 11.10 |
| L28 | Aspergillus flavipes | 5.90 | 5.73 | 5.82 |
| L29 | Aspergillus sp. | 7.40 | 6.40 | 6.90 |
| L30 | Aspergillus sp. | 8.58 | 7.27 | 7.92 |
| L31 | Aspergillus sp. | 6.22 | 5.75 | 5.98 |
| L32 | Penicillium sp. | 21.09 | 14.28 | 17.69 |
| L33 | Aspergillus oryzae | 7.71 | 7.48 | 7.59 |
| L34 | Aspergillus sp | 6.88 | 6.28 | 6.58 |
| L35 | Aspergillus sp. | 7.00 | 6.16 | 6.58 |
| L36 | Aspergillus niger strain | 8.52 | 6.70 | 7.61 |
| L37 | Penicillium oxalicum | 14.52 | 9.53 | 12.03 |

TABLE 3-continued

Scoring of Strain Performance (Hydrolysis Potential) Using the Weighted Sum Model (Wsm)

| Identity | Name | Sum of weights for ALK | Sum of weights for AFEX | Average sum of weights |
|---|---|---|---|---|
| L38 | Aspergillus sp. | 7.66 | 6.84 | 7.25 |
| L39 | Penicillium citrinum strain | 6.50 | 6.25 | 6.37 |
| L40 | Aspergillus sp. | 8.07 | 6.34 | 7.20 |
| L41 | Trichoderma atroviride | 15.02 | 10.77 | 12.89 |
| L42 | Penicilliuimfuniculosum | 54.96 | 64.63 | 59.80 |
| L43 | Trichoderma reesei | 4.95 | 5.55 | 5.25 |
| L44 | Trichoderma reesei | 4.76 | 4.69 | 4.73 |
| L45 | Aspergillus niger | 4.68 | 6.21 | 5.45 |

The re-evaluation of the strain's identity through its internal transcribed spacer (ITS1-5.8S-ITS2) region sequences revealed 100% similarity to ITS1-5.8S-ITS2 sequences from *Penicillium pinophilum*, *Penicillium allahabadense*, *Acremonium cellulolyticus*, *Talaromyces pinophilus*, *T. cellulolyticus* and *Talaromyces verruculosus*.

Example-7: Identifying and Evaluating Total Proteins from the Most Performing Strain SDS-PAGE Analysis:

Sodium dodecyl sulfate (SDS)-polyacrylamide gels (12%) were prepared and proteins were separated via SDS-polyacrylamide gel electrophoresis (PAGE). Proteins of the gel were stained with Coomassie blue R-250. The molecular mass under denaturing conditions was determined with reference standard proteins.

Protein Preparation for LC-MS/MS Analysis:

One hundred micrograms of total protein from the most performing strain was separated by one dimensional (1D) electrophoresis prepared and stained as described above. The 1D electrophoresis lane was cut into 15 pieces based on the protein banding pattern (FIG. 1). Each fraction was further diced into 1 mm by 1 mm cubes and transferred into 1.5 mL microfuge tubes. In-gel digestion was carried out. Gel pieces were first destained with 100 mM ammonium bicarbonate/acetonitrile (1:1 vol/vol), followed by addition of 50 µl of 10 mM dithiothreitol and incubation at 56° C. for 45 minutes. After cooling, the supernatant was removed, and the samples were alkylated in the presence of 50 µl of 55 mM iodoacetamide at room temperature in the dark for 30 minutes. Gel pieces were washed with 100 mM ammonium bicarbonate/acetonitrile (1:1, vol/vol) for 15 minutes after which enough acetonitrile was added to cover the gel particles. The gels were then dried in a vacuum speed concentrator. In-gel digestion was performed overnight with 200 ng of trypsin gold-mass spectrometry grade. The resulting peptides were extracted twice with 50% acetonitrile in 0.1% formic acid for 20 minutes followed by 70% acetonitrile in 0.1% formic acid for 20 minutes. These two peptide extracts were pooled, dried in a vacuum speed concentrator. Dried peptides from each fraction were dissolved in 0.1% formic acid.

Data Acquisition:

All experiments were performed on an OrbitrapVelos Pro equipped with nano-LC Easy nLC-1000. For liquid chromatography, separation was performed with a flow rate of 300 nl/min on a C-18 pre-column (Acclaim PepMap, 75 µm×2 cm, 3 µm, 100 A°) followed by analytical column (Acclaim PepMap, 50 µm×15 cm, 2 µm, 100 A°). The peptides were separated using a gradient of 5% solvent B to 35% B in 25 min followed by sharp increase to 90%, then retention of 90% for 3 min followed by 5% aqueous phase for 5 min. Solvent A was aqueous solution in 0.1% formic acid, and solvent B was 100% acetonitrile in 0.1% formic acid. The eluted peptides were injected into the mass spectrometer and the MS1 data were acquired in full scan mode at 60000 resolutions with mass range from 350-2000 Da. Data were acquired using the Xcalibur software package. Top 20 precursors were allowed to fragment using CID (collision induced dissociation) in Ion trap with collision energy of 35 in a data dependent acquisition. The lock mass option (polydimethylcyclosiloxane; m/z 445.120025) enabled accurate mass measurement in both the MS and MS/MS modes.

Evaluating Protein Interaction Dynamics in *Penicillium funiculosum* by Non-Denaturing Size Exclusion Chromatography and Mass Spectrometry Based Quantitative Proteomics (SEC-MS):

To separate the crude *Penicillium funiculosum* into its natural associating partners, crude secretome (20 mg) prepared as described above was loaded in a HiLoad 16/600 Superdex 200 pg pre-packed XK columns using a NGC™ Medium-Pressure Chromatography System. Absorbance was monitored at 280 nm. Elution was performed with 50 mM sodium acetate buffer PH 5.0 containing 150 mM NaCl at an optimal flow rate of 0.5 ml/min. Protein from the individual fractions were subjected to SDS-PAGE as described above but were silver stained. Based on the observed protein banding pattern sub fractions were pooled into five groups (pools A to E). Protein from pooled fractions were concentrated using Vivaspin columns with a 5 kDa MWCO and were subsequently run on 12% Laemmli SDS-PAGE and stained with Coomassie Blue R-250. The relative concentration of proteins in the pooled fractions was also determined using the BCA method. About 20 µg of protein from each pool were reduced and alkylated followed by a subsequent acetone precipitation. The obtained pellets were re-suspended in 50 mM NH4HCO3 and trypsin digested in-solution 48. The resulting peptides were extracted and treated as described above for MS/MS analysis. The other portions of the protein pools were used for biomass hydrolysis/saccharification. The apparent molecular mass of the fractions was estimated by gel filtration on the same column as described above calibrated with a GE Healthcare high-molecular-weight (HMW) gel filtration calibration kit (GE Healthcare). The molecular masses of standards used were ovalbumin (44 kDa), conalbumin (75 kDa), aldolase (158 kDa), ferritin (440 kDa) and blue dextran (2,000 kDa). Other portion of the pools were evaluated for their biomass saccharification potential with respect to the saccharification potential of the crude secretome The total reducing sugar concentration were determined as described in the biomass saccharification section above. The biomass hydrolysis efficiency of the pools was expressed as percentage hydrolysis using the formula below:

$$\% \text{ hydrolysis} = 100 \times \frac{\text{Amount of reducing sugar released by respective fractions}}{\text{Amount of reducing sugar released by the crude secretome}}$$

Figure 2:
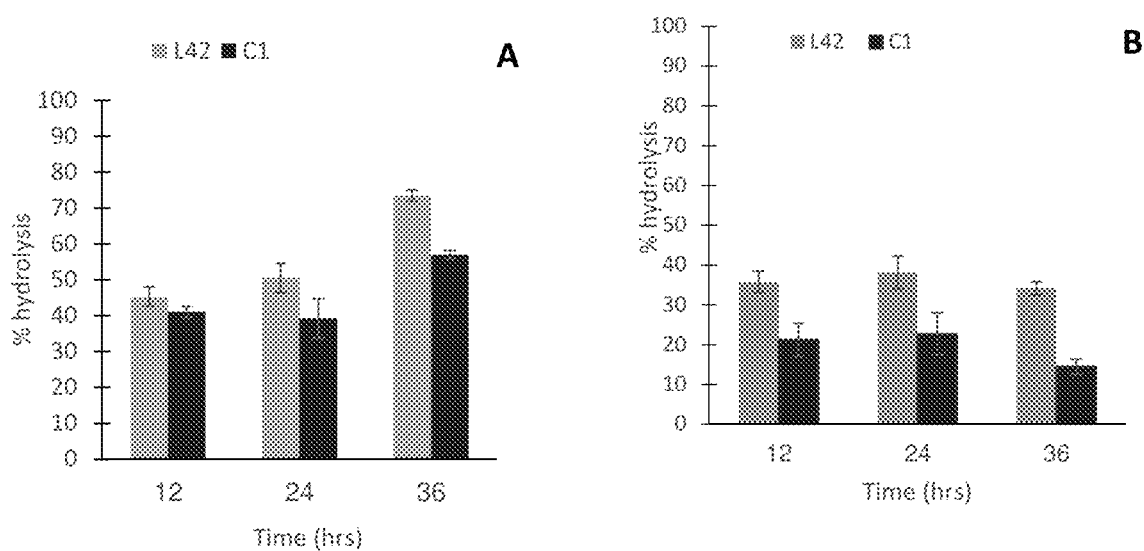
FIG. 2 depicts biomass degradation kinetics of *Penicillium funiculosum* (NCIM 1228) in relation to commercial cellulase cocktail—Advanced Enzyme Ltd formulation (C1). Panel A represents the hydrolysis dynamics on sodium hydroxide pretreated wheat straw while panel B represents the hydrolysis dynamics on AMM=Ammonium pre-treated wheat straw. The amount of reducing sugar released was quantified using 3, 5-Dinitrosalicylic acid (DNSA) assay. The different enzyme preparations were loaded at 0.2 filter paper unit (FPU) per gram of biomass. Biomass loading was at 5% dry weight loading. Values plotted were means±standard error of means of three independent experiments.

Example-8: Comparative Evaluation of Biomass Saccharification and the Lignocellulolytic Enzyme Activities of *Penicillium funiculosum* Secretome Produced During Submerged Cultivation To further ascertain the biomass hydrolysing capability of the strain, the efficiency of the crude enzyme obtained under the cellulase inducing conditions were compared with that of a commercial cellulase preparation both at low enzyme and high enzyme loading. Protein loading was normalised based on the filter paper units of the respective enzyme. *P. funiculosum* secretome saccharification activities out performs that of the commercial enzymatic mixture both on sodium hydroxide and ammonia pre-treated wheat straws at 50° C. (FIG. 2). The observation describing it as an excellent source of biomass degrading enzymes; with capabilities exceeding that of *Trichoderma reesei* which has been the hub for most commercial cellulase preparation. A closer look at the cellulase (endoglucanase, cellobiohydrolyase, β-glucosidase), hemicelluase (xylanase, beta-xylosidase) and polysaccharide monoxygenase (GH61) activities of the fungus' secretome in relation to the commercial enzyme revealed a significantly higher cellobiohydrolase, β-glucosidase and LPMO activities per mg of protein produced by the fungus; while the commercial enzyme cocktail showed a significantly higher endoglucanase, β-xylosidase and endoxylanase activities per mg of protein.

Example-9: Overview of *Penicillium funiculosum* (NCIM 1228) Secretome

Secretome analysis, apart from being an excellent method to understand the biological mechanisms of lignocellulose degradation, is a valuable tool in the search for new enzymes or interesting enzyme complexes in the biofuels field. To understand the repertoire of proteins in the "most performing" secretome of the fungus *Penicillium funiculosum* NCIM1228 and their relative abundance, a proteomic study was undertaken comparing the obtained mass spectrometry spectra against in house predicted proteins (11213 target sequences) obtained from the draft genome sequence of the fungus available. These analyses led to the identification of 195 proteins, validated at 1% FDR.

It is noteworthy to mention that the numbers of proteins identified in the present invention were significantly higher than the number reported in the previous report where only 50 proteins were unambiguously identified in Rovabio™ (a commercial cocktail from *Penicillium funiculosum*). It was possible to identify more proteins from the secretome experiments because the acquired mass spectra were queried against predicted proteins from the draft genome sequence of the strain available, while in the earlier work the protein identity was through homology search with public fungi database. The high number of detected proteins may also attributable to the possibly higher induction of a large subset of enzymes during cultivation as well as the sensitivity of the mass spectrometer used. To assign functions of the identified protein the Blast2GO suite was used. Most of the functions were assigned from the genus *Talaromyces* (Table 3) which is the sexual state of *Penicillium*. However in instances where certain proteins were described as hypothetical protein, putative functions were assigned through pair wise similarity function between identified proteins had earlier developed a method to partition biological data into groups of similar objects through Transitivity Clustering.

Figure 3:
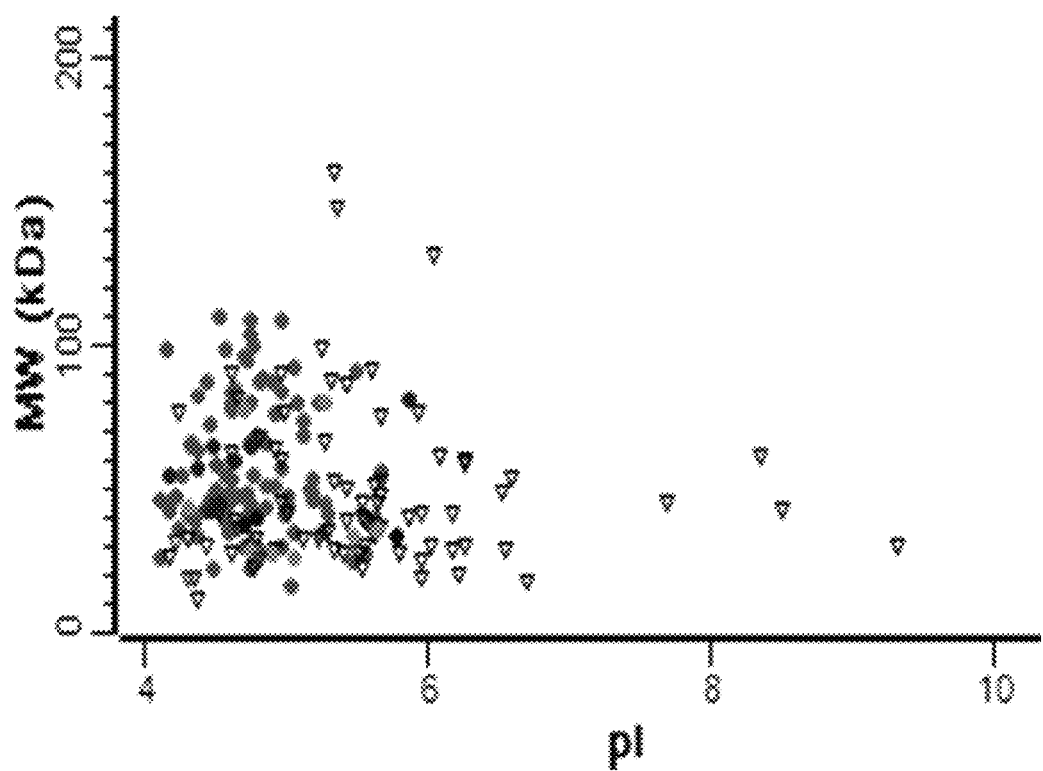
FIG. 3 depicts a plot of molecular weight against the isoelectric point (pI). The molecular weights of proteins validated at 1% were profiled against their theoretical pI. Data points in circle are CAZymes with red colored indicating glycoside hydrolases (GHs); blue colored—Auxilliary Activities related enzymes (AAs); ash colored—Carbohydrate Esterases (CEs); black colored—Polysaccharide Lyases (PLs). All other non CAZymes are represented as black colored open inverted triangles. Proteins associated with polysaccharide binding are with brown colored open inverted triangles.
Figure 4:
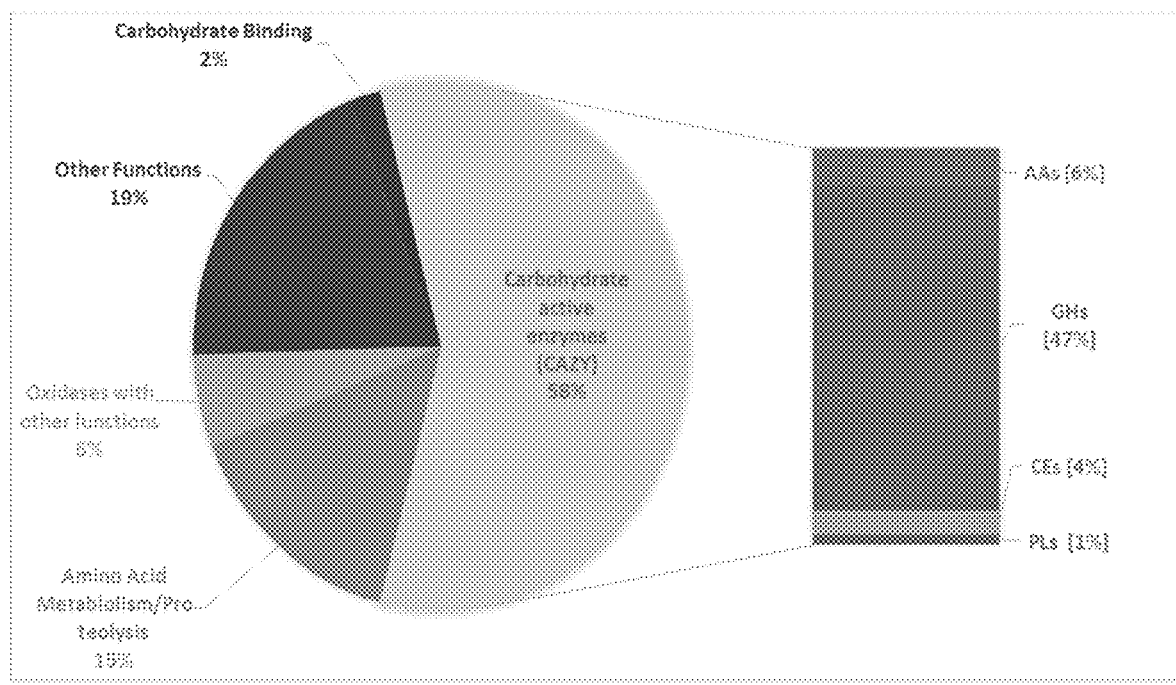
FIG. 4 depicts functional classification of proteins identified in secretome of *Penicillium funiculosum* (NCIM 1228).

The results showed that the molecular weights of the identified proteins were in the range of 11-150 kDa, with the exception of a putative histone acetylase complex subunit Paf400 showing a molecular weight of 439 kDa, while most of the carbohydrate active proteins were with pI within the acidic range (FIG. 3). Of the validated proteins, only 38% were confirmed to have N-terminal Sec-dependent secretion secretory signals in silico. Functional categorization of the validated proteins based on CAZy database indicated that 58% of the total proteins (113 proteins) were CAZymes out of which 47% (92 proteins representing 38 families) were identified as glycoside hydrolases, 6% (11 proteins representing 5 families) as performing auxiliary activities, 4% (7 proteins representing 6 families) as carbohydrate esterases and a 1% (3 proteins representing only the PL1 family) as polysaccharide lyases. Other non CAZymes identified include proteins involved in carbohydrate binding (2%), amino acid metabolism or proteolysis (15%), oxidases with other functions (6%), hypothetical or proteins with other functions (19%) (FIG. 4)

Figure 5:
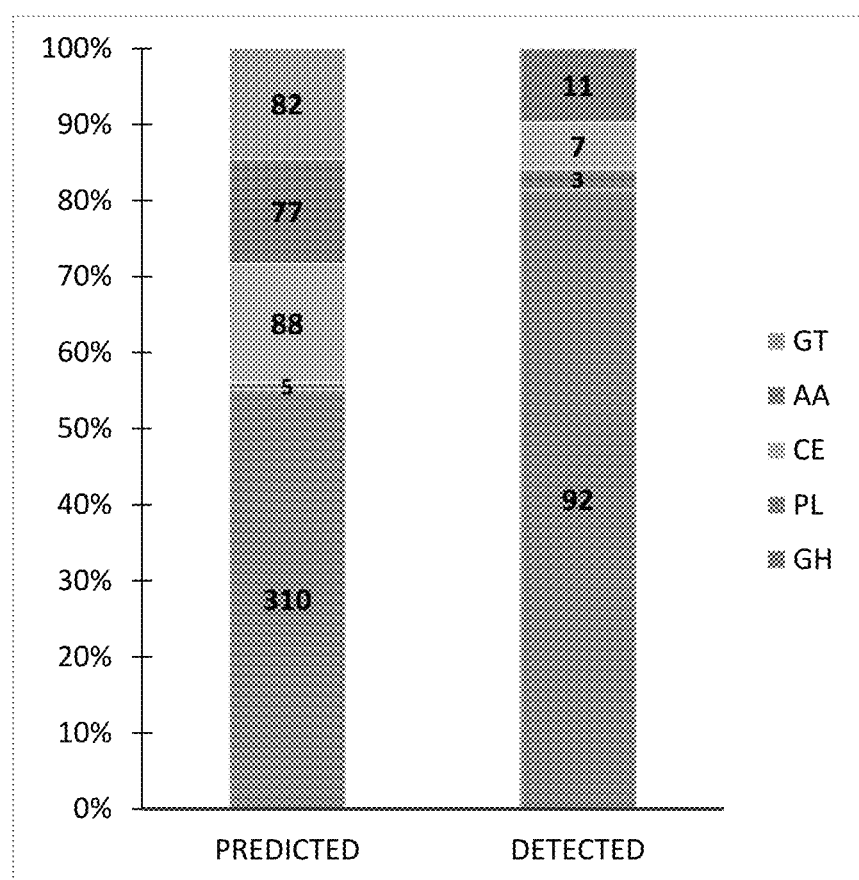
FIG. 5 depicts the number and distribution of predicted CAZymes obtained from the draft genome sequence versus CAZymes detected in the most performing secretome of *Penicillium funiculosum* NCIM 1228. Values in each category represent the actual number of CAZymes. GT=Glycosyl Transferases, AA=Auxiliary Activities, CE=Carbohydrate Esterases, PL=Polysaccharide Lyases and GH=Glycoside Hydrolases.

A comparative evaluation of all possible CAZymes from the draft genome sequence as against those was detected in the secretome of Penicillium funiculosum is presented in (FIG. 5). Although only 20% of the possible CAZymes were detected through the proteomic experiment, however it is noted that proteins belonging to the class copper-dependent lytic polysaccharide monooxygenases (LPMOs)—AA9, cellobiohydrolase II—GH6, cellobiohydrolase I and endoglucanase GH7, xylanase—GH10, β-hexosaminidase GH20, endo-β-1,4-galactanase—GH53, α-L-arabinofuranosidase—GH62, α-trehalase—GH65, β-glucuronyl hydrolase—GH88 and pectin lyase—PL1 present were identified in the secretome at 100% of the possible magnitude in the genome of the fungus.

Other identified proteins at an upward of 40% of the possible proteins in the genome included: lignin peroxidase—AA2, acetyl xylan esterase—CE2, β-glucosidase and β-xylosidase—GH3, β-mannosidase and endoglucanase—GHS, xylanase—GH11, endoglucanase—GH12, α-galactosidase—GH27, glucosylceramidase—GH30, β-galactosidase—GH35, α-glucuronidase—GH67, α-1,3-glucanase—GH71, β-1,3-glucanosyltransglycosylase—GH72, α-mannosidase—GH92 and an hypothetical protein of the class GH79. Many of the identified glycoside hydrolases possessed additional carbohydrate binding modules (CBMs) belonging to 8 different families. The identified CBMs may be grouped into Type A CBMs (predominantly CBM1 which acts on crystalline cellulose) and type B (CBMs from families 6, 18, 20, 24, 42, 43 and 46 which acts linear oligosaccharide chains in the less crystalline region of cellulose). CBMs increase cellulase concentration on the surface of the insoluble substrate, recognize the specific site in the substrates, and induce cellulose disruption, all of which facilitate cellulase catalytic activity. These arrays of core cellulases, hemicelluases as well as accessory enzymes detected in the "most performing secretome" possibly explaining the observed excellent biomass hydrolysis from the fungus. Interestingly, most of the detected proteins have been reported to be the major players in biomass hydrolysis. Of notable point to be mentioned is the detection of LPMOs (formerly GH61) belonging to the AA9 family and the confirmation of such through enzyme assay. A cellobiose dehydrogenase (CDH) of the CAZy family AA3 was equally detected in the secretome. This may be the possible synergistic partner (electron donor) for the AA9 protein. It was found that the fungi strain of the present invention possess 25 genes encoding proteins of the class AA3 but only one gene encoding AA9 protein. In general, the CDH/PMO system helps to improve the degradation of cellulose in combination with cellulases. The diversity of enzymes related to biomass hydrolysis detected in the "most performing secretome" gives credence to the axiom that complex substrates leads to lead to the induction of more complex lignocellulolytic cocktails.

Example-10: Quantitative Analysis of Carbohydrate Active Proteins in the Secretome of Penicillium funiculosum To gain an insight into the relative abundance of the respective proteins present in the "most performing" secretome, spectrum abundance indexes were estimated using the Normalized Spectrum Abundance Factor (NSAF).

The result shows the preponderance of cellobiohydrolase 1 (CBH1) and cellobiohydrolase II (CBH II) belonging to the GH7 and GH6 families respectively. This predominance of cellobiohydrolases is similar to reports from Trichoderma reesei strains although the proportions are at lesser magnitudes. While CBHs typically represent up to 90-95% of the total secreted protein in Trichoderma reesei with CBH1 making up 50-60% and CBH II approx. 20% of the total cellulases, it was only observed a cumulative CBHs abundance totaling 15% with CBH1 approx. 10% and CBHII 5% of the identified proteins. CBH1 from Penicillium species are known to have higher specificity as well as more resistant to inhibition by cellobiose. This may suggest why they were produced at lesser magnitudes. There equally may be the presence of other enzymes working in tandem with the CBHs to synergistically deconstruct biomass. In the experiment, other highly abundant classes of enzymes making up the approximately 60% of total proteins include: endoglucanases (GHS, 7, 12 & 17), β-glucosidase (GH3), endoxylanases (GH10, GH11), glucoamylase (GH15), extracellular cell wall glucanase (GH16), arabinofuranosidase (GH62), Lytic polysaccharide monooxygenase (AA9), ferulic acid esterase (CE1), swollenin-like proteins, hydrophobic surface binding-like protein (HSbA) and immunoglobulin E binding protein. It is worth stating that non-hydrolytic accessory proteins such as swollenin-like proteins, hydrophobic surface binding-like protein (HSbA) and immunoglobulin E binding proteins make up about 10% of the total secreted proteins. Their high abundance could point to their role in biomass hydrolysis by Penicillium funiculosum. The synergism between cellulases and/or other enzymes for complete lignocellulose hydrolysis is well documented. Swollenin shows disruptive activity toward various cellulosic substrates, presumably through their ability to disrupt hydrogen bonds, thereby reducing cellulose crystallinity and increasing cellulase accessibility, while hydrophobic surface binding protein A (HsbA) is involved in the sensing of, or physical association with, hydrophobic surfaces and promotion of substrate degradation. In Aspergillus oryzae, HsbA gets adsorbed to hydrophobic surfaces such as—Polybutylene succinate-co-adipate (PBSA) in the presence of NaCl or $CaCl_2$ and promotes its degradation via a cutin-degrading esterase (CutL1 polyesterase). So, it may be performing similar function(s) in Penicillium funiculosum, mediating degradation via recruiting hydrolases to the surface of lignocellulosic biomass.

Example-11: Evaluating Protein Interaction Dynamics in Penicillium funiculosum Secretome by Non-Denaturing Size Exclusion Chromatography and Mass Spectrometry Based Quantitative Proteomics (SEC-MS)

Figure 6:
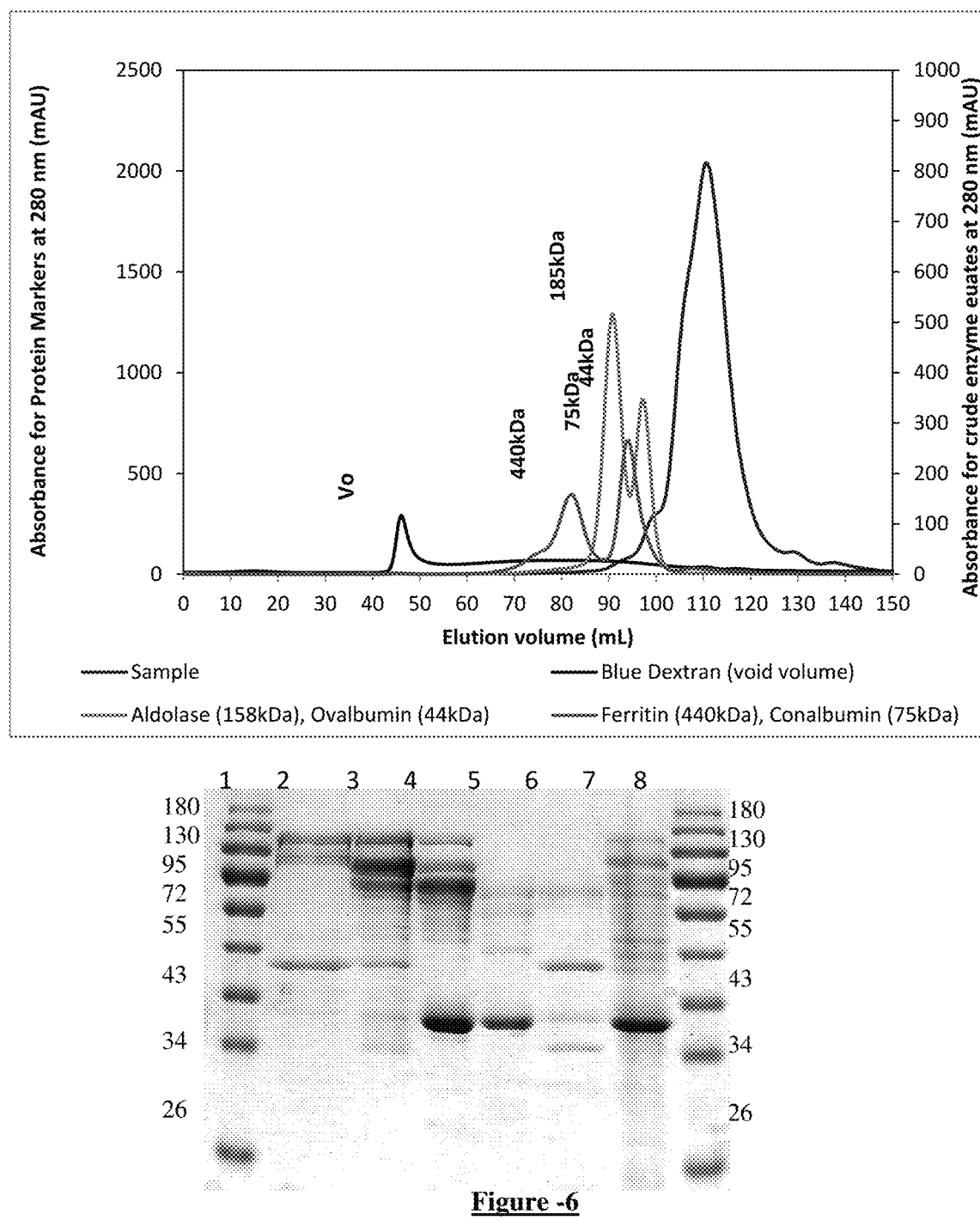
FIG. 6 depicts the non-denaturing size exclusion fractionation of *Penicillium funiculosum* crude enzyme (NCIM 1228). Panel A represents a chromatogram of SEC-fractionated secretome (~20 mg of proteins) eluted with 50 mM sodium acetate buffer PH 5.0 containing 150 mM NaCl. The elution volume, measured in mL, is represented on the x-axis. UV absorbance is represented on the y-axis. Protein standards of known molecular weights (ferritin (440 kDa), aldolase (158 kDa), conalbumin (75 kDa) and ovalbumin (44 kDa) were loaded onto the same column. For the crude enzyme sample, no significant protein absorbance was detected before 83 mL as monitored by the online UV detector at 280 nm as such the collected fractions were discarded. Fractions showing similar banding pattern were pooled together as follows: pool A=F1-F5 (83.32-93.34 mL), pool B=F6-F8 (93.34-99.35 mL), pool C=F9-F12 (99.35-107.36 mL), pool D=F13-F16 (107.36-115.37 mL) and pool E=F17-F25 (115.37 mL-135.36 mL). Panel B represents the banding pattern of different SEC fraction pools of *P. funiculosum* crude. Protein load was at 15 μg per lane. Lanes 1 to 8 represents protein marker, pooled fractions A to E; and equal load of *P. funiculosum* crude protein respectively.

The secretion in large quantities of varieties of carbohydrate active proteins has been one of the reasons while filamentous fungi have been in the mainstay of cellulase research. Having validated a total of 195 proteins of which a greater proportion has carbohydrate-related functions (FIG. 4), the main interest was to understand the protein interaction dynamics in the secretome of *P. funiculosum*. It was intended to enrich for "useful vs junk proteins" that could potentiates improved biomass saccharification. To this end, we subjected the crude secretome was subjected through a non-denaturing size exclusion chromatography (FIG. 6). Size-exclusion chromatography (SEC) being a well-established technique used to separate proteins and protein complexes in solution on the basis of their rotational cross section and size; offers a comparative advantage of understanding and characterizing soluble protein dynamics in their native conformation and on a system-wide scale when coupled with downstream mass spectrometry. Fractions eluting after 83 mL were subjected to a reducing SDS-PAGE and silver stained. Results showed that the majority of proteins in the crude secretome of *P. funiculosum* eluted over a broad range between 90 mL to 130 mL which literally could translate to the predominance of low molecular weight proteins in the secretome when compared to the elution volume of the molecular weight standards. However the protein profile/banding pattern revealed by SDS-PAGE indicates the presence of multiple proteins with molecular weight ranging from approx. 10 kDa to 130 kDa. While size exclusion chromatography have been used to estimate the relative size of individual proteins and/complexes, the molecular weights of glycoproteins or non-globular proteins may not correlate well to the calibration curves established for globular proteins by the Calibration Kit proteins. However, these standards provide a general size indication. When proteins interact to form multimers, their sizes and shapes are altered and this affect their migration pattern during size exclusion chromatography. In addition, the possibility of protein-resin interactions cannot be ruled out as the gel filtration medium is made from carbohydrate, and the crude enzyme being rich in carbohydrate-binding proteins could be interacting with the resin. To this end, sub-fractions showing similar banding pattern were pooled on reducing SDS-PAGE together into five pools viz: A to E (FIG. 7) for downstream quantitative proteomics investigations and biomass hydrolysis.

For proteomic investigations, the resulting pools were digested with trypsin, and then the peptides analyzed via LC-MS/MS. The MS data files were analyzed and peptides associated with each fraction identified and quantitated using MaxQuant. The relative protein abundance in each of the sub-fraction pools were estimated and normalised using the iBAQ approach. A total of 86 unique proteins were validated at 1% FDR by MaxQuant across the protein pools of which 31, 40, 29, 17 and 13 proteins were exclusively associated with protein pools A to E respectively (Table 4).

TABLE 4

The distribution of validated proteins across the different SEC pools

| Names | Total | Elements |
|---|---|---|
| Group A, Group B, Group C, Group D, Group E | 1 | Cellobiohydrolase 1 (GH7-CBM1) |
| Group A, Group B, Group C, Group D | 1 | cellobiohydrolase II |
| Group B, Group C, Group D, Group E | 1 | endoglucanase GH5-CBM1; beta-1,4-xylanase GH10-CBM1; endoglucanase GH45 |
| Group A, Group B, Group C | 2 | beta-glucosidase (GH1); glucoamylase (GH15-CBM20) |
| Group B, Group C, Group D | 2 | beta-D-glucoside glucohydrolase (GH3); alpha-L-arabinofuranosidase (GH54-CBM42) |
| Group C, Group D, Group E | 3 | endoglucanase GH5-CBM1; beta-1,4-xylanase GH10-CBM1; endoglucanase GH45 |
| Group A, Group B | 14 | beta-glucosidase [GH3]; pyridoxine biosynthesis protein; FerredoxinNAD-reductase; spindlepolebody protein; Catalase-peroxidase [AA2]; mucin family signaling protein Msb2; DnaJ domain protein; proteasome component Pre9; GPI anchored protein; Catalase B; Chitinase [GH18-CBM18]; antigenic mitochondrial protein HSP60; alpha-trehaloseglucohydrolase [GH65] |
| Group B, Group C | 4 | alpha-amylase [GH13-CBM20]; isoamyl alcohol oxidase, putative [AA7]; glucoamylase precursor [GH15-CBM20]; alpha-L-arabinofuranosidase A [GH51] |
| Group C, Group D | 1 | Glycoside Hydrolase family 18 protein [GH18] |
| Group D, Group E | 1 | alpha-L-arabinofuranosidase [GH62-CBM1] |
| Group A | 13 | beta-glucosidase [GH3]; pyridoxine biosynthesis protein; Ferredoxin NAD-reductase; spindle polebody protein; Catalase-peroxidase [AA2]; mucin family signaling protein Msb2; DnaJ domain protein; proteasome component Pre9, putative; GPI anchored protein; Catalase B; Chitinase [GH18-CBM18]; antigenic mitochondrial protein HSP60; alpha-trehalose glucohydrolase [GH65] |

TABLE 4-continued

The distribution of validated proteins across the different SEC pools

| Names | Total | Elements |
| --- | --- | --- |
| Group B | 15 | carboxylesterase; transaldolase; Beta-galactosidase [GH35]; 1,3-beta-glucanosyltransferase[GH72-CBM43]; feruloylesterase; glutaminase GtaA; alpha-amylase; swollenin; alpha-1,2-mannosidase [GH92]; cyanate hydratase; SUN domain protein (Uth1); Aminopeptidase 2; Xaa-Pro aminopeptidase pepP; aminotransferase, class V; 1,3-beta-glucanosyltransferase Gel2 [GH72] |
| Group C | 14 | glycogen synthase kinase; xylosidase; predicted protein; Rhamnogalacturonase A [GH28]; endoglucanase 5 [GH5-CBM1]; IgE-binding protein; pectin lyase 1 [PL1]; Cytochrome nitrite reductase; GMF family protein; putative FAD binding domain protein; Hydrophobic surface binding protein A; alpha galactosidase; FAD-dependent oxidase, putative [AA7]; endoglucanase [GH5-CBM46] |
| Group D | 7 | alpha-L-arabinofuranosidase precursor, [GH62]; alpha-galactosidase [GH27 - CBM1]; Glycoside Hydrolase family 11 protein [GH11]; xylanase [GH11]; aldo/keto reductase; hypothetical protein; 40S ribosomal protein S18 |
| Group E | 7 | glycosyl hydrolase family 43 protein [GH43]; conserved hypothetical protein [CE2-CBM1]; xylanase [GH11-CBM1]; Carbohydrate esterase [CE3-CBM1]; Xyloglucanase [GH74-CBM1]; xylanase [GH11-CBM1]; acetyl xylan esterase [CE5-CBM1] |

Figure 7:
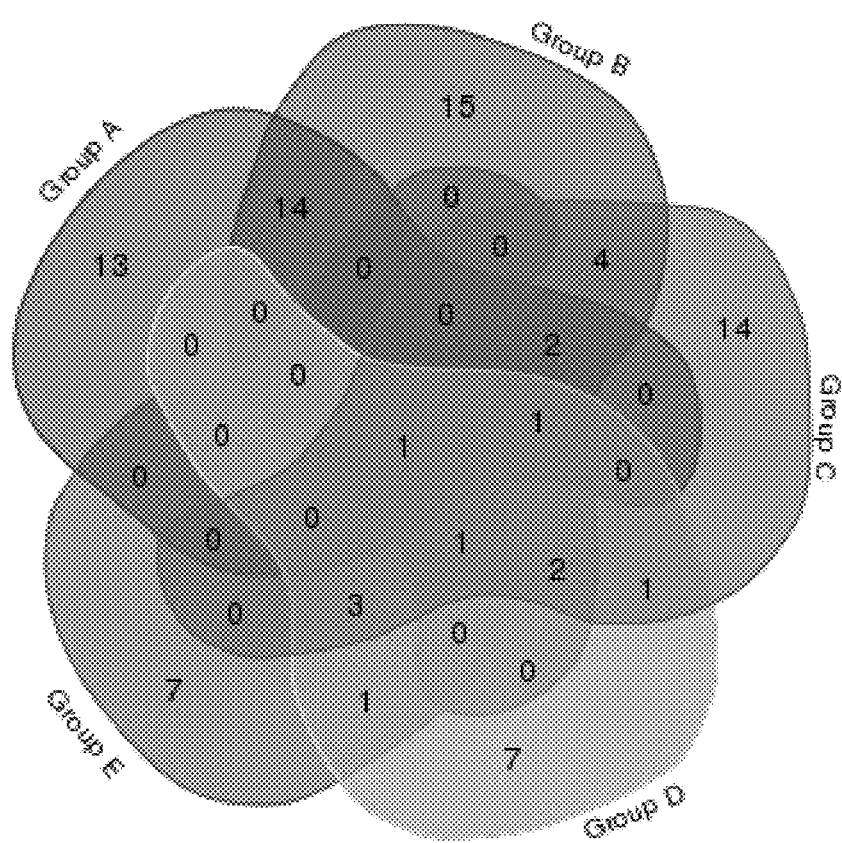
FIG. 7 depicts a Venn diagram describing the relative distribution of differentially associating protein across SEC fraction pools of *Penicillium funiculosum* NCIM 1228.
Figure 8:
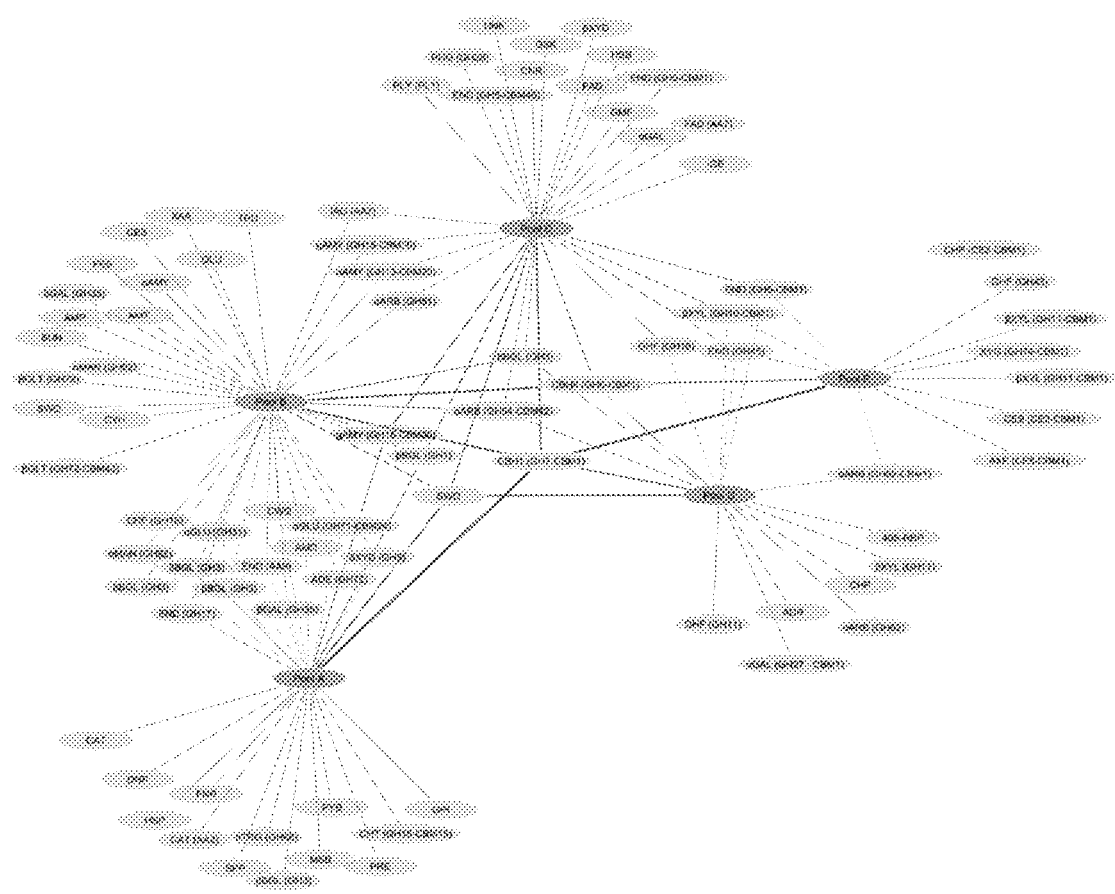
FIG. 8 depicts a network representation of the Protein Interaction Dynamics across SEC fraction pools. The various proteins are represented as nodes while interactions as edges. The weight of the edge represents the edge betweenness of the nodes.
Figure 9:
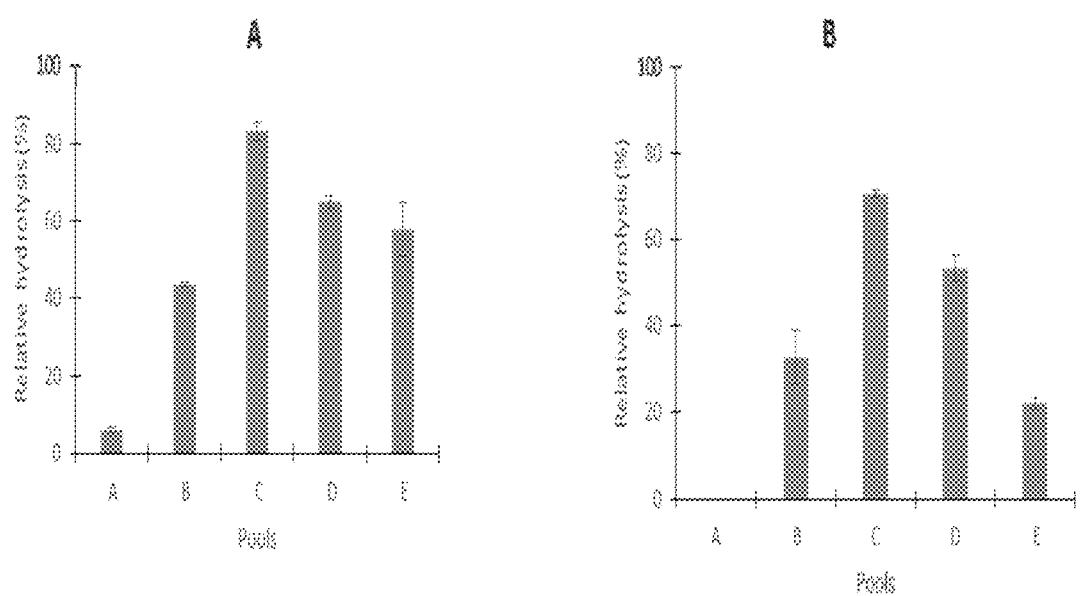
FIG. 9 depicts the biomass hydrolysis of different pools from SEC fractions of *P. funiculosum* (NCIM 1228) secretome. The biomass hydrolysis potential of the different pools (differentially associating protein groups following separation under native SEC) expressed as a percentage of the total with respect to the crude protein. The amount of the total reducing sugar was estimated through the dinitrosalicylic acid (DNSA) method. Panels A and B represent the observed hydrolysis pattern on sodium hydroxide and ammonium pre-treated wheat straw respectively. Hydrolysis was carried out at 50° C. with 20 mg of protein samples per gram of dry weight biomass.
Figure 10:
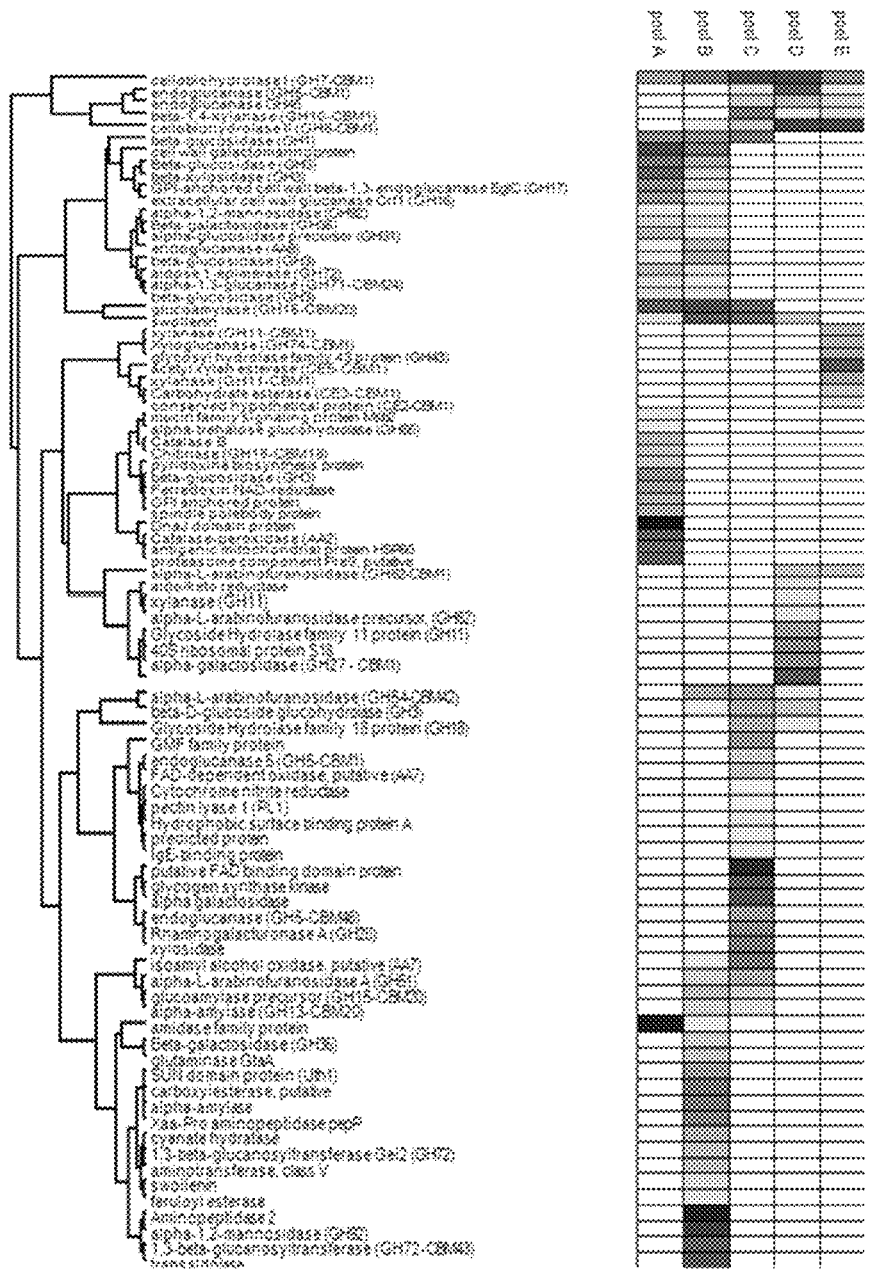
FIG. 10 depicts hierarchical clustering of proteins per fraction pool showing the abundance of differentially associating proteins. The hierarchical clustering was performed on log transformed iBAQ intensities using Euclidean distance and complete linkage.
Figure 11:
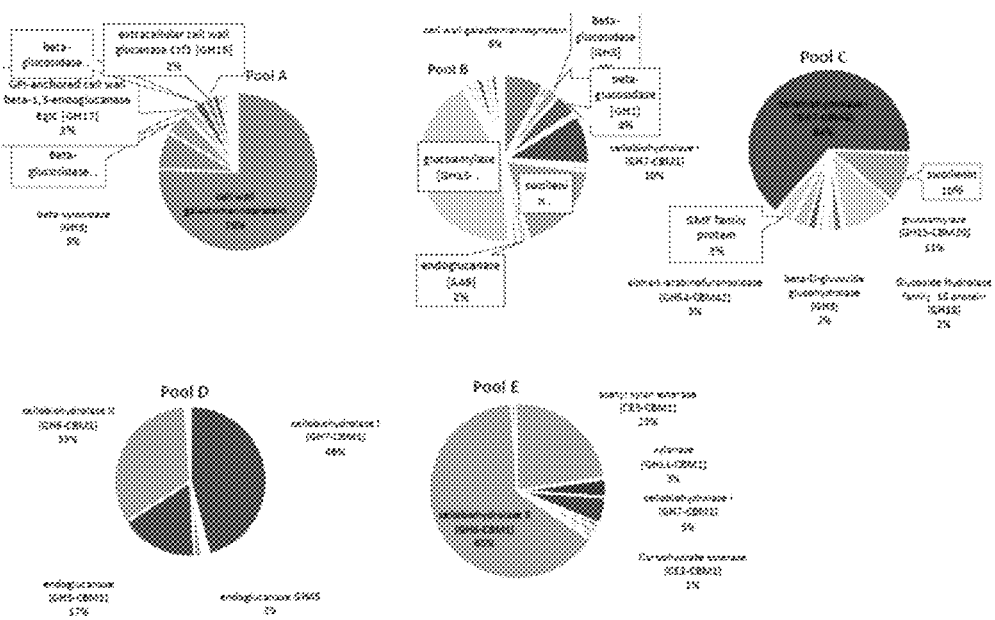
FIG. 11 depicts the stoichiometries of major proteins in the different SEC fraction pools of *Penicillium funiculosum* NCIM 1228.
Figure 12:
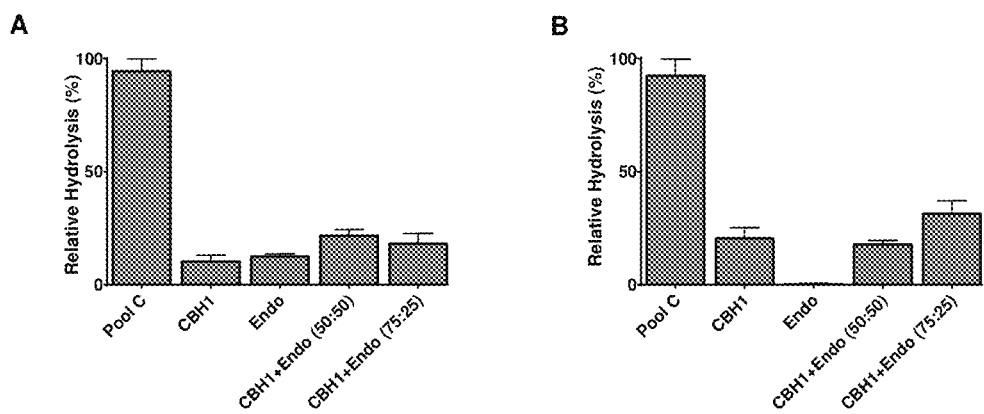
FIG. 12 depicts the synergistic activity of pool C, being the composition of the present invention.

An overview of the protein distribution and network across the respective groups is shown in FIGS. 7 and 8. It observed that the different proteins present in the respective pools tend to differentially associate with each other with some proteins being represented in more than one contiguous protein pool. For instance, cellobiohydrolase 1 (GH7-CBM1) was found across the protein pools A to E. Swollenin was found in pools A to D, cellobiohydrolase II (GH6-CBM1) found in pools B, C, D and E; beta-glucosidase (GH1) & glucoamylase (GH15-CBM20) present in pools A, B & C; beta-glucosidase (GH3) & alpha-L-arabinofuranosidase (GH54-CBM42) present in pools B, C &D and endoglucanase GH5-CBM1,beta-1,4-xylanase GH10-CBM1 and endoglucanase GH45 present in pools C,D &E. A hierarchical clustering to give a visual representation of the distribution and the relative abundance of the various detected proteins across the pools is given in FIG. 10. The detection of a protein across multiple pools suggests they differentially associate with multiple proteins. In evaluating the interaction dynamics of the human interactome when stimulated with epidermal growth factor (EGF) using SEC coupled with mass spectrometry, it was noted that proteins frequently participate in more than one complex or in similar complexes with different stoichiometries. This is similar to what was observed with the different stoichiometries of the different proteins occurring across the multiple pools (FIGS. 10 and 11). While SEC is expected to give a continuum of proteins with regular molecular weight pattern in adjacent pools, it was observed that the exclusive co-elution of certain low molecular weight proteins less than 20 kDa in pools B, C and D but conspicuously missing in pool E where they should have naturally eluted based on their low molecular weight (FIGS. 6, 7 and 8). This suggests certain of the protein are interacting with some other proteins in the pool. Of a seemingly interest is the presence of certain low molecular weight proteins—IgE-binding like (18 kDa), Hydrophobic surface binding protein A (HsbA) protein (17 kDa) exclusively co-eluting with other higher molecular weight proteins in pool C. Their relative abundance and exclusive co-elution in protein pool C where it was observed that the highest percentage of sugar release (FIG. 9) gives credence to the earlier suggestion that they may be enhancing the deconstruction of biomass through synergy with core cellulases. This is of great importance when the stoichiometries of proteins in the different fraction pools are put in perspective. The pool C (FIG. 9) is an illustration of the composition of the present invention. The composition of the present invention as shown in pool C (FIG. 12) is synergistic. Furthermore two components of Pool C, namely, CBH1 (GH7-CBM1) and Endoglucanase (GH5-CBM1), were separated and analyzed for biomass hydrolysis individually or in combination with (a) sodium hydroxide and (b) ammonium hydroxide pre-treated wheat straws and the results are presented at FIG. 12. From FIG. 12, it can be seen that further separation of components of Pool C will result in significant drop in ability of enzyme to hydrolyse the biomass, demonstrating that composition of the present invention is synergistic.

Example-12: Obtaining the Various Components of the Composition of the Present Invention The components of the composition of the present invention were selected from the various protein pools. The composition of the present invention may be obtained by combining the components of the composition. The composition of the present invention for biomass hydrolysis comprising Cellobiohydrolase I (GH7-CBM1) in the range of 50%-75%, beta-D-glucoside glucohydrolase (GH3) in the range of 1%-4%, xylanase (GH11-CBM1) in the range of 1%-6%, swollenin in the range of 7%-13%, GMF family protein in the range of 1%-5%, IgE-binding protein in the range 1%-3%, Hydrophobic surface binding protein A in the range 1%-3%, endoglucanase (GH5-CBM1) in the range of 2%-25%, LPMO (AA9) in the range of 1%-5%. Optionally, the composition further comprises, cellobiohydrolase II (GH6-CBM1) in the range of 25%-40%, endogluconase GH45 in the range of 0.50%-2.5%, alpha-L-arabinofuranosidase in the range of 2%-5%, acetyl xylan esterase (CE5-CBM1) in the range of (15%-30%), carbohydrate esterase (CE3-CBM1) in the range of 0.30%-2%, Glycoside Hydrolase family 18 protein (GH 18) in the range of 1%-4%, glucoamylase (GH15-CBM20) in the range of 8%-15%,

The invention claimed is:

1. A composition for hydrolysis of biomass comprising;
   a. Cellobiohydrolase I (GH7-CBM1) in the range of 50%-75%, beta-D-glucosideglucohydrolase (GH3) in the range of 1%-4%, xylanase (GH11-CBM1) in the range of 1%-6%, swollen in in the range of 7%-13%, GMF family protein in the range of 1%-5%, IgE-binding protein in the range 1%-3%, Hydrophobic surface binding protein A in the range 1%-3%, endoglucanase (GH5-CBM1) in the range of 2%-25%, and LPMO (AA9) in the range of 1%-5%,
   b. optionally, comprising, cellobiohydrolase II (GH6-CBM1) in the range of 25%-40%, endoglucanase GH45 in the range of 0.50%-2.5%, alpha-L-arabinofuranosidase in the range of 2%-5%, acetyl xylan esterase (CE5-CBM1) in the range of (15%-30%), carbohydrate esterase (CE3-CBM1) in the range of 0.30%-2%, Glycoside Hydrolase family 18 protein (GH 18) in the range of 1%-4%, and glucoamylase (GH15-CBM20) in the range of 8%-15%,
   wherein, the composition is obtained from *Penicillium funiculosum* (NCIM1228).

2. A method for producing/obtaining the composition as claimed in claim 1, comprising:
   a) collecting and selecting the potential cellulase degrading fungi;
   b) culturing the fungi obtained in step (a) and obtaining the secretome;
   c) selecting secretome based on enzyme activity;
   d) selecting and ranking of secretome based on biomass hydrolyzing capabilities;
   e) identifying preferred strains;
   f) analysing secretome of the preferred strain; and
   g) obtaining/identifying the composition as claimed in claim 1.

3. The method of producing the composition as claimed in claim 2, wherein, the cellulase degrading fungi is obtained from decaying plant, agricultural waste dump sites, fungi culture repository and related sources; and is selected by culturing in media selected from the group comprising Brain-heart infusion agar, Czapek's agar, Inhibitory mold agar, Mycobiotic agar, Potato Dextrose Agar, Sabouraud's Heart Infusion agar, Sabouraud's dextrose agar, Potato flake agar, CMC-Trypan blue agar preferably CMC-Trypan blue agar and subculturing in a media selected form the group comprising Brain-heart infusion agar, Czapek's agar, Inhibitory mold agar, Mycobiotic agar, Potato Dextrose Agar, Sabouraud's Heart Infusion agar, CMC-Trypan blue agar, Sabouraud's dextrose agar, Potato flake agar, preferably Potato Dextrose Agar.

4. The method of producing the composition as claimed in claim 2, comprises calculating an enzyme Index as a function of the fungus growth (diameter) in relation to the diameter of the observed clear zones (halos) on agar media plate wherein the enzymatic index of the fungi is greater than or equal to 1.

5. The method of producing the composition as claimed in claim 2, wherein, the fungi are cultured from cellulase inducing medium and the secretome is obtaining by centrifugation.

6. The method of producing the composition as claimed in claim 2, wherein, secretomes have enzyme activity in the range of β-glucosidase (3.71+−0.009 U/mg), endoglucanase (3.14+−0.088 U/mg), cellobiohydrolase (0.20+−0.019 U/mg), β-xylosidase (0.21+−0.005 U/mg), endoxylanase (3.39+−0.103 U/mg), polysaccharide monooxygenases (0.05+−0.0003 U/mg) and filter paper activity (0.64+−0.05 FPU/mg).

7. The method of producing the composition as claimed in claim 2, wherein, the secretomes have biomass mass hydrolyzing capabilities in the range of 70% to 100% on wheat straw.

8. The method of producing the composition as claimed in claim 2, wherein, the preferred strains are identified by PCR using primers.

9. The method of producing the composition as claimed in claimed in 2, wherein, secretome were analysed and selected on biomass hydrolysis.

10. The method of producing/obtaining the composition as claimed in claim 2, wherein, the composition comprises:
  a. Cellobiohydrolase I (GH7-CBM1) in the range of 50%-75%, beta-D-glucoside glucohydrolase (GH3) in the range of 1%-4%, xylanase (GH11-CBM1) in the range of 1%-6%, swollenin in the range of 7%-13%, GMF family protein in the range of 1%-5%, IgE-binding protein in the range 1%-3%, Hydrophobic surface binding protein A in the range 1%-3%, endoglucanase (GH5-CBM1) in the range of 2%-25%, and LPMO (AA9) in the range of 1%-5%,
  b. optionally, comprising, cellobiohydrolase II (GH6-CBM1) in the range of 25%-40%, endoglucanase GH45 in the range of 0.50%-2.5%, alpha-L-arabinofuranosidase in the range of 2%-5%, acetyl xylan esterase (CE5-CBM1) in the range of (15%-30%), carbohydrate esterase (CE3-CBM1) in the range of 0.30%-2%, Glycoside Hydrolase family 18 protein (GH 18) in the range of 1%-4%, and glucoamylase (GH15-CBM20) in the range of 8%-15%.

11. The method of producing the composition as claimed in claim 2, wherein, the composition is obtained from the potential cellulase degrading fungi is *Penicillium funiculosum* (NCIM1228).

* * * * *